United States Patent
Sharma et al.

(10) Patent No.: US 11,339,153 B2
(45) Date of Patent: May 24, 2022

(54) COMPOUNDS USEFUL IN MODULATING THE FARNESOID X RECEPTOR AND METHODS OF MAKING AND USING THE SAME

(71) Applicant: Inorbit Therapeutics AB, Billdal (SE)

(72) Inventors: Rajiv Sharma, Fremont, CA (US);
Lambertus Benthem, Billdal (SE);
Robert Judkins, Mölndal (SE)

(73) Assignee: Inorbit Therapeutics AB, Billdal (SE)

( * ) Notice: Subject to any disclaimer, the term of this patent is extended or adjusted under 35 U.S.C. 154(b) by 0 days.

(21) Appl. No.: 17/265,266

(22) PCT Filed: Aug. 6, 2019

(86) PCT No.: PCT/US2019/045266
§ 371 (c)(1),
(2) Date: Feb. 2, 2021

(87) PCT Pub. No.: WO2020/033382
PCT Pub. Date: Feb. 13, 2020

(65) Prior Publication Data
US 2021/0309656 A1 Oct. 7, 2021

Related U.S. Application Data

(60) Provisional application No. 62/716,015, filed on Aug. 8, 2018.

(51) Int. Cl.
*C07D 261/08* (2006.01)
*C07D 451/06* (2006.01)
*C07D 413/12* (2006.01)

(52) U.S. Cl.
CPC ......... *C07D 451/06* (2013.01); *C07D 261/08* (2013.01); *C07D 413/12* (2013.01)

(58) Field of Classification Search
CPC .... C07D 261/08; C07D 451/10; A61K 31/42; A61K 31/46
USPC ................ 546/130; 548/247; 514/304, 380
See application file for complete search history.

(56) References Cited

FOREIGN PATENT DOCUMENTS

| DE | 2545964 A1 * | 1/2013 | ........... C07D 413/14 |
|----|---|---|---|
| EP | 2545964 A1 | 1/2013 | |
| WO | 2011020615 A1 | 2/2011 | |
| WO | 2012087519 A1 | 6/2012 | |
| WO | 2016096115 A1 | 6/2016 | |
| WO | 2016096116 A1 | 6/2016 | |
| WO | 2017218379 A1 | 12/2017 | |
| WO | 2018039386 A1 | 3/2018 | |

OTHER PUBLICATIONS

Berge et al. "Pharmaceutical Salts" Journal of Pharmaceutical Sciences, 66:1-19 (1977).
Bundgaard, Hans "(C) Means to enhance penetration: (1) Prodrugs as a means to improve the delivery of peptide drugs" Journal of Drug Deliver Reviews, 8(1):1-38 (1992).
Crawley, Matthew "Farnesoid X receptor modulators: a patent review" Expert Opinion on Therapeutic Patents, 20(8):1047-1057 (2010).
Forman et al. "Identification of a Nuclear Receptor That Is Activated by Farnesol Metabolites" Cell, 81(5):687-693 (1995).
Gege et al. "Nonsteroidal FXR Ligands: Current Status and Clinical Applications" Handbook of Experimental Pharmacology, 256:167-205 (2019).
Holt et al. "Definition of a novel growth factor-dependent signal cascade for the suppression of bile acid biosynthesis" Genes & Development, 17(13):1581-1591 (2003).
Inagaki et al. "Fibroblast growth factor 15 functions as an enterohepatic signal to regulate bile acid homeostasis" Cell Metabolism, 2(4):217-225 (2005).
Lew et al. "The Farnesoid X Receptor Controls Gene Expression in a Ligand- and Promoter-selective Fashion" The Journal of Biological Chemistry, 279(10):8856-8861 (2004).
Makishima et al. "Identification of a Nuclear Receptor for Bile Acids" Science, 284(5418):1362-1365 (1999).
Mangelsdorf et al. "The RXR Heterodimers and Orphan Receptors" Cell, 83(6):841-850 (1995).
Nielsen et al. "Glycolamide esters as biolabile prodrugs of carboxylic acid agents: Synthesis, stability, bioconversion, and physicochemical properties" Journal of Pharmaceutical Sciences, 77(4):285-298 (1988).
Regan et al. "Acyl Glucuronides: The Good, The Bad and The Ugly" Biopharmaceutics & Drug Disposition, 31:367-395 (2010).
Sepe et al. "Farnesoid X receptor modulators 2014-present: a patent review" Expert Opinion on Therapeutic Patents, 28(5):351-364 (2018).
Shipkova et al. "Acyl glucuronide drug metabolites: Toxicological and analytical implications" Therapeutic Drug Monitoring 25(1):1-16 (2003).
Ballatore et al. "Carboxylic Acid (Bio)Isosteres in Drug Design" ChemMedChem, 8(3):385-395 (2013).
Burgos-Lepley et al. "Carboxylate bioisosteres of gabapentin" Bioorganic & Medicinal Chemistry Letters, 16:2333-2336 (2006).
Gnaim et al. "Tagging the Untaggable: A Difluoroalkyl-Sulfinate Ketone-Based Reagent for Direct C—H Functionalization of Bioactive Heteroarenes" Bioconjugate Chemistry, 27:1965-1971 (2016).

(Continued)

*Primary Examiner* — Jeffrey H Murray
(74) *Attorney, Agent, or Firm* — Myers Bigel, P.A.

(57) ABSTRACT

Provided are compounds that can act as a modulator of a farnesoid X receptor (FXR) and that can be useful in the treatment of diseases and/or disorders associated with the FXR such as bile acid related disorders, metabolic syndrome, type-2-diabetes, hyperlipidemia, hypertriglyceridemia, primary biliary cirrhosis (PBC), fatty liver disease, nonalcoholic steatohepatitis (NASH), inflammatory autoimmune diseases, Crohn's disease, multiple sclerosis, atherosclerosis, kidney disorders (including chronic kidney disease), hepatic and colon cancers, and other disorders. The compounds are in the class of sulfinic acid compounds and can be an enantiomer, stereoisomer, tautomer, solvate, hydrate, prodrug, metabolite, or pharmaceutically acceptable salt thereof. Compositions including such compounds are also provided along with methods for preparing compounds of the present invention and their use.

17 Claims, 1 Drawing Sheet

(56) References Cited

OTHER PUBLICATIONS

International Preliminary Report on Patentability corresponding to International Patent Application No. PCT/US2019/045266 (13 pages) (dated Oct. 29, 2020).
International Search Report and the Written Opinion of the International Searching Authority corresponding to International Patent Application No. PCT/US2019/045266 (21 pages) (dated Dec. 19, 2019).
Tully et al. "Discovery of Tropifexor (LJN452), a Highly Potent Non-bile Acid FXR Agonist for the Treatment of Cholestatic Liver Diseases and Nonalcoholic Steatohepatitis (NASH)" Journal of Medicinal Chemistry, 60:9960-9973 (2017).

* cited by examiner

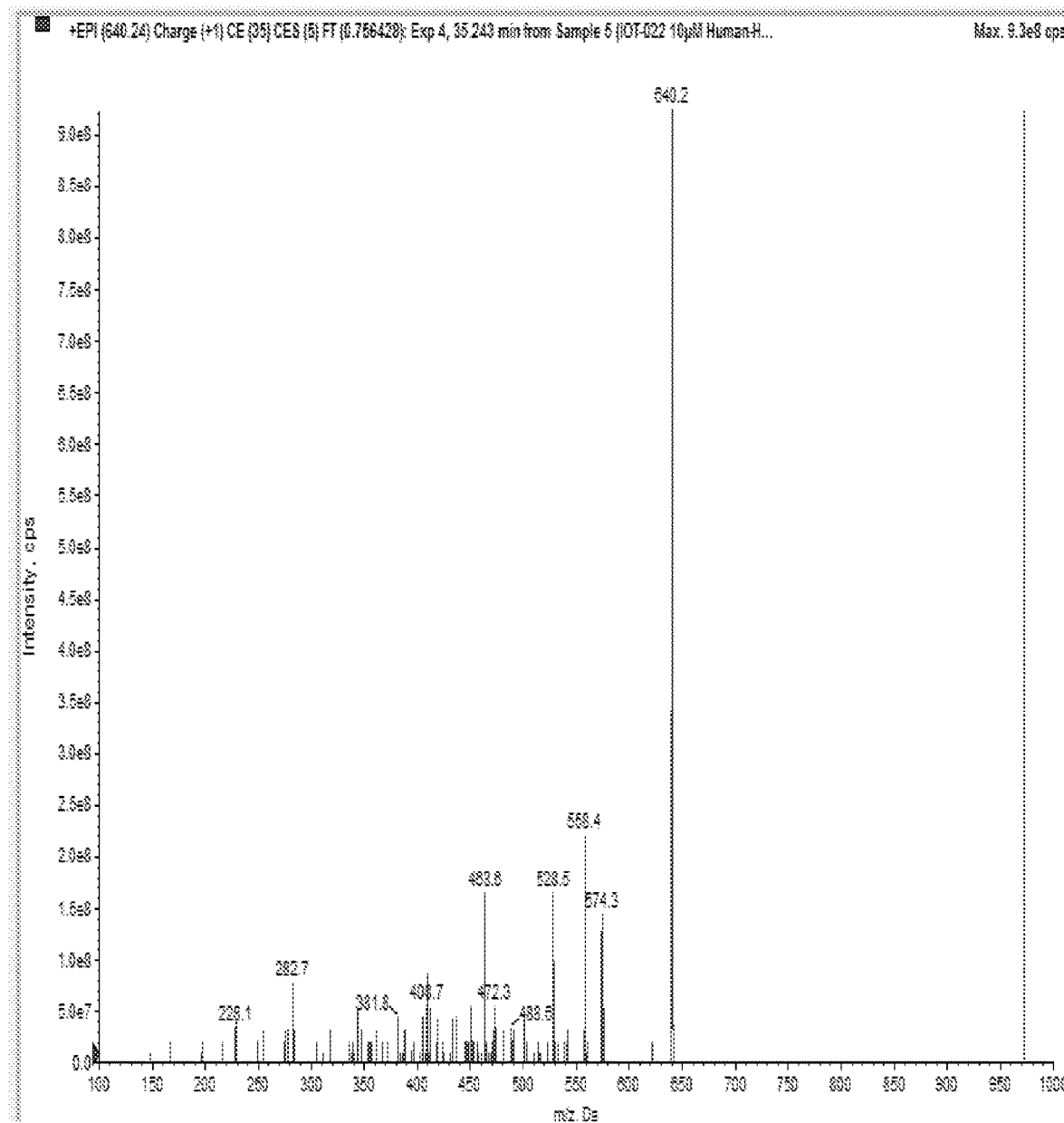

COMPOUNDS USEFUL IN MODULATING THE FARNESOID X RECEPTOR AND METHODS OF MAKING AND USING THE SAME

RELATED APPLICATION DATA

This application claims the benefit of U.S. Provisional Patent Application Ser. No. 62/716,015, filed Aug. 8, 2018, the disclosure of which is incorporated herein by reference in its entirety.

FIELD

The present invention relates to compounds that can act as modulators of a farnesoid X receptor (FXR) and that can be useful in the treatment of diseases and/or disorders associated with the FXR. In some embodiments, the present invention relates to compounds and compositions that modulate a FXR and methods for their preparation and use.

BACKGROUND

The farnesoid X receptor is a member of the nuclear hormone receptor superfamily. The FXR functions as a heterodimer with the retinoid X receptor (RXR) and binds to response elements in the promoter region of target genes to regulate gene transcription. Studies have shown that FXR plays an important role in control of enterohepatic circulation of bile acids, bile acid synthesis, and secretion and bile acid uptake into hepatocytes. This aspect has been exploited by many researchers for finding appropriate drug targets for the treatment of NASH/NAFLD.

The farnesoid X receptor is an orphan nuclear receptor initially identified from a rat liver cDNA library (B M. Forman, et al., Cell, 1995, 81(5), 687-693) that is most closely related to the insect ecdysone receptor. FXR is a member of the nuclear receptor superfamily of ligand-activated transcription factors that includes receptors for the steroid, retinoid, and thyroid hormones (D J. Mangelsdorf, et al., Cell, 1995, 83(6), 841-850). FXR is expressed in various tissues including liver, kidney, intestine, colon, ovary, and adrenal gland (see Forman et al, Cell 81:687-693, 1995; Lu et al, J. Biol. Chem., 17:17, 2001) and is a key regulator of cholesterol homeostasis, triglyceride synthesis and lipogeneis (Crawley, Expert Opinion Ther. Patents (2010), 20(8): 1047-1057).

The relevant physiological ligands of FXR are bile acids (D. Parks et al., Science, 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. Beyond controlling intracellular gene expression, FXR seems to also be involved in paracrine and endocrine signaling by upregulating the expression of the cytokine Fibroblast Growth Factor (J. Holt et al., Genes Dev., 2003, 17(13), 1581-1591; T. Inagaki et al., Cell Metab., 2005, 2(4), 217-225).

Activation of the FXR has the potential to be a treatment for a range of diseases including bile acid related disorders, metabolic syndrome, type-2-diabetes, hyperlipidemia, hypertriglyceridemia, primary biliary cirrhosis (PBC), fatty liver disease, nonalcoholic steatohepatitis (NASH), inflammatory autoimmune diseases, Crohn's disease, multiple sclerosis, atherosclerosis, kidney disorders (including chronic kidney disease), hepatic and colon cancers, and other disorders. Although numerous FXR modulators are known and have been disclosed (for recent examples see, A. Zampella et al., Expert Opinion Ther. Patents (2018), 28(5): 351-364), there is still a need for the development of novel and potent compounds for the treatment and prevention of disease.

The listing or discussion of an apparently prior-published document in this specification should not necessarily be taken as an acknowledgement that the document is part of the state of the art or is common general knowledge.

SUMMARY

One aspect of the present invention is directed to compounds represented by Formula I, an enantiomer, stereoisomer, tautomer, solvate, hydrate, prodrug, amino acid conjugate, metabolite, or pharmaceutically acceptable salts thereof:

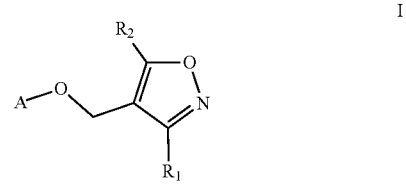

wherein:

$R_1$ is a $C_{3-10}$ cycloalkyl, phenyl or pyridyl, each of which is optionally substituted with 1-3 $R_{1a}$;

each $R_{1a}$ is independently selected from the group consisting of a halogen, $C_{1-6}$ alkyl, halo$C_{1-6}$ alkyl, $C_{1-6}$ alkoxy, halo$C_{1-6}$ alkoxy and cyclopropyl;

$R_2$ is a $C_{1-3}$ alkyl, halo$C_{1-3}$ alkyl or cyclopropyl, each of which is optionally substituted with a $C_{1-3}$ alkyl or halo$C_{1-3}$ alkyl;

A is selected from:

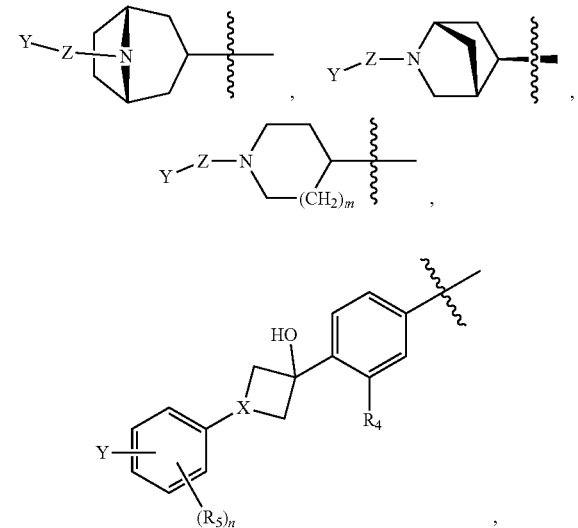

-continued

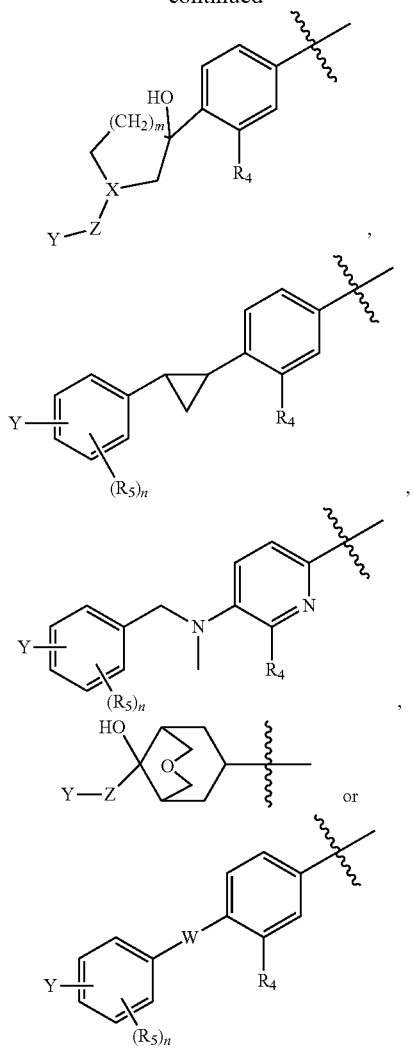

Y is —S(O)OH or —S(O)₂OH, optionally wherein Y is —S(O)OH;

Z is phenyl or a 5-10 membered monocyclic or bicyclic heteroaryl containing 1-2 heteroatoms selected from N, O and S, wherein the phenyl or 5-10 membered monocyclic or bicyclic heteroaryl is optionally substituted with 1-2 $R_6$;

W is a 4 or 5 membered monocyclic heterocycle or heteroaryl containing 1-3 heteroatoms from N, O and S;

each $R_6$ is independently selected from the group consisting of a halogen, $C_{1-6}$ alkyl, halo$C_{1-6}$ alkyl, $C_{1-6}$ alkoxy, halo$C_{1-6}$ alkoxy, and cyclopropyl;

X is N or CH;

$R_4$ is a H, $C_{1-6}$ alkyl, $C_{1-6}$ alkoxy, halo$C_{1-6}$ alkyl, $C_{3-6}$ cycloalkyl, or halogen;

each $R_5$ is independently selected from the group consisting of a $C_{1-6}$ alkyl, $C_{3-6}$ cycloalkyl, halo$C_{1-6}$ alkyl, $C_{1-6}$ alkoxy, halo$C_{1-6}$ alkoxy and halogen;

m is an integer of 0, 1 or 2; and n is an integer of 0, 1, 2 or 3;

which compounds, enantiomers, stereoisomers, tautomers, solvates, hydrates, prodrugs, amino acid conjugates, metabolites, and pharmaceutically acceptable salts are referred to hereinafter as "the compounds of the invention". In some embodiments, the invention provides a compound of Formula I, wherein $R_2$ is cyclopropyl. In some embodiments, the invention provides a compound selected from the group consisting of:

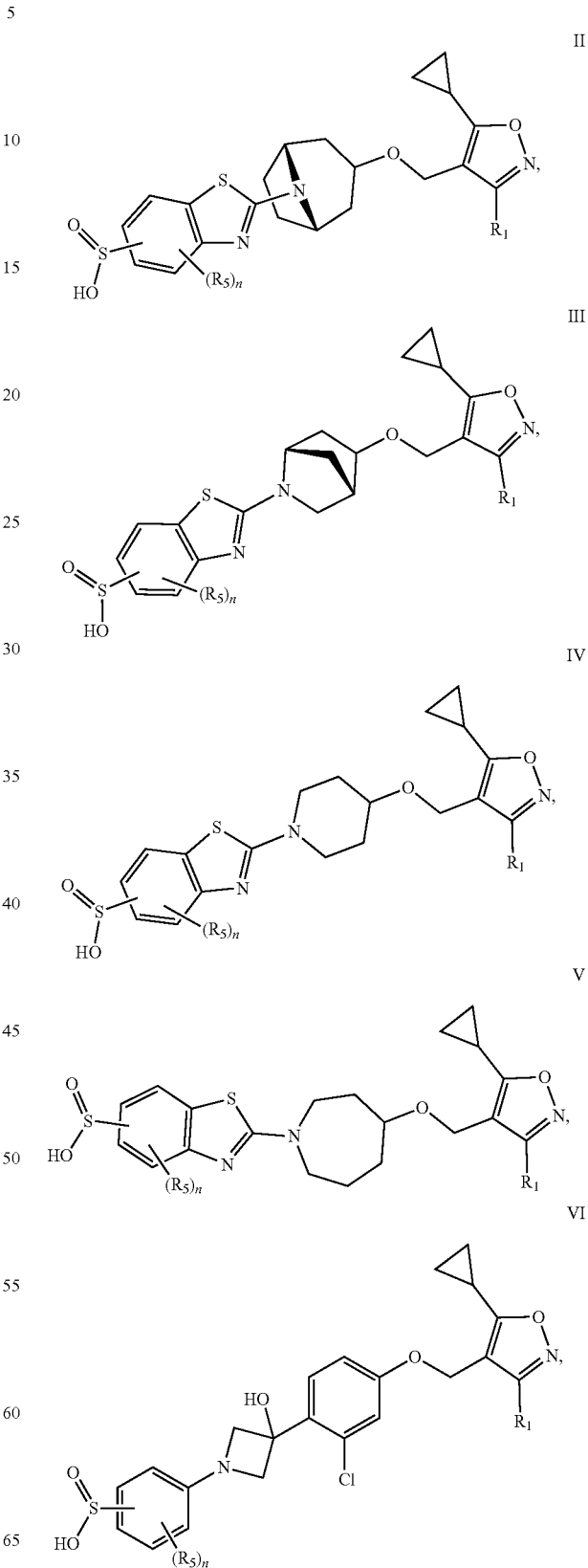

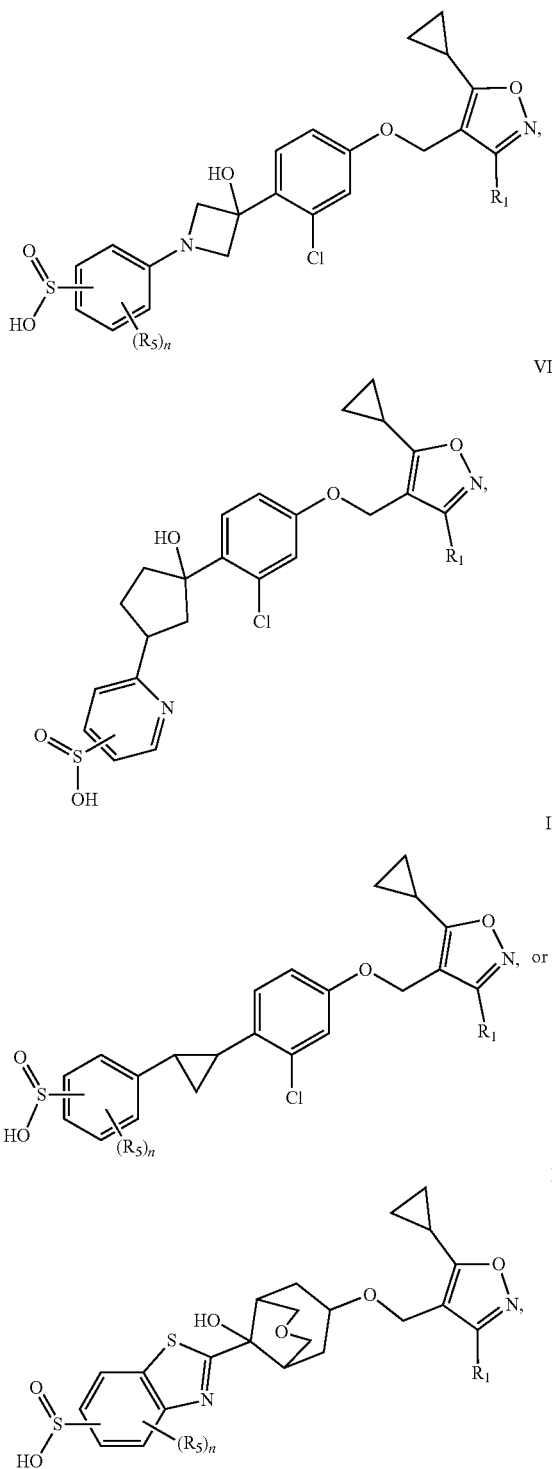

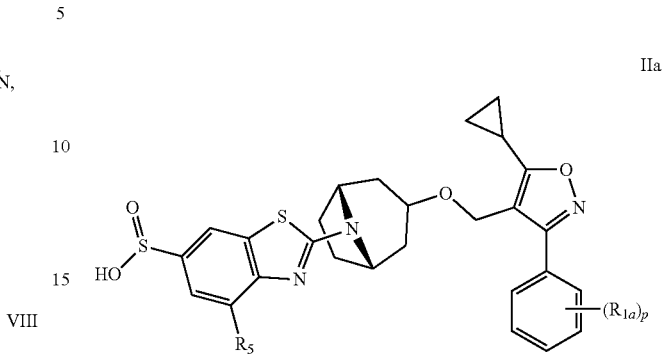

wherein $R_1$, $R_5$ and n are each as defined above.

In some embodiments, the invention provides a compound of Formula I-X, wherein $R_1$ is phenyl that is optionally substituted with 1-3 $R_{1a}$, wherein each $R_{1a}$ is independently selected from the group consisting of a halogen, $C_{1-6}$ alkyl, halo$C_{1-6}$ alkyl, $C_{1-6}$ alkoxy, and halo$C_{1-6}$ alkoxy, optionally wherein each $R_{1a}$ is independently selected from the group consisting of a halogen, methoxy, methyl, trifluoromethyl, trifluoromethoxy, and difluoromethoxy.

In some embodiments, the invention provides a compound having a structure represented by Formula IIa:

wherein each $R_{1a}$ is independently selected from the group consisting of a halogen, trifluoromethyl, trifluoromethoxy and difluoromethoxy; $R_5$ is methyl, methoxy, fluoro or trifluoromethoxy; and p is an integer of 0 or 1, or an enantiomer, stereoisomer, tautomer, solvate, hydrate, prodrug, amino acid conjugate, metabolite, or pharmaceutically acceptable salt thereof.

In some embodiments, the invention provides a compound selected from the group consisting of sodium 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-sulfinate, sodium 2-((1R,3r,5S)-3-((5-cyclopropyl-3-(2-(trifluoromethoxy)phenyl)isoxazol-4-yl)methoxy)-8-azabicyclo[3.2.1]octan-8-yl)-4-methylbenzo[d]thiazole-6-sulfinate, sodium 3-(3-(2-chloro-4-((5-cyclopropyl-3-(2,6-dichlorophenyl)isoxazol-4-yl)methoxy)phenyl)-3-hydroxyazetidin-1-yl)benzenesulfinate, sodium 4-(3-(2-chloro-4-((5-cyclopropyl-3-(2,6-dichlorophenyl)isoxazol-4-yl)methoxy)phenyl)-3-hydroxycyclobutyl)benzenesulfinic acid, sodium 4-(2-(2-chloro-4-((5-cyclopropyl-3-(2,6-dichlorophenyl)isoxazol-4-yl)methoxy)phenyl)cyclopropyl)benzenesulfinate, and any combination thereof.

Another aspect of the present invention is directed to a method of modulating a FXR. The method comprises administering to a subject in need thereof an effective amount of a compound of the present invention (e.g., a compound of Formula I or a pharmaceutically acceptable salt, hydrate, solvate, prodrug, stereoisomer, or tautomer thereof).

Another aspect of the present invention is directed to a method of activating a FXR. The method comprises administering to a subject in need thereof an effective amount of a compound of the present invention (e.g., a compound of Formula I or a pharmaceutically acceptable salt, hydrate, solvate, prodrug, stereoisomer, or tautomer thereof).

Another aspect of the present invention is directed to a method of treating and/or preventing a disease and/or disorder. In some embodiments, the disease and/or disorder is a bile acid related disorder, metabolic syndrome, type-2 diabetes, diabetic nephropathy, hyperlipidemia, hypertriglyceridemia, obesity, liver cirrhosis, primary biliary cirrhosis (PBC), primary sclerosing cholangitis (PSC), fatty liver disease, nonalcoholic steatohepatitis (NASH), nonalcoholic fatty liver disease (NAFLD), alcoholic liver disease, chemotherapy associated steatohepatitis (CASH), hepatitis B, inflammatory autoimmune diseases, inflammatory bowel disease, Crohn's disease, ulcerative colitis, proctitis, pouchitis, Celiac's Disease, bile acid diarrhea, multiple sclerosis, atherosclerosis, kidney disorders (including chronic kidney disease), cancer including hepatic cancers, colon cancers and breast cancers, and other disorders. The method comprises administering to a subject in need thereof a therapeutically effective amount of a compound of the present invention (e.g., a compound of Formula I or a pharmaceutically acceptable salt, hydrate, solvate, prodrug, stereoisomer, or tautomer thereof)) or a pharmaceutical composition comprising said compound of the present invention.

A further aspect of the present invention is directed to a pharmaceutical composition comprising a compound of the present invention (e.g., a compound of Formula I or a pharmaceutically acceptable salt, hydrate, solvate, prodrug, stereoisomer, or tautomer thereof) and a pharmaceutically acceptable carrier. The pharmaceutical composition may further include an excipient, diluent, and/or surfactant.

Another aspect of the present invention relates to a compound of the present invention (e.g., a compound of Formula I or a pharmaceutically acceptable salt, hydrate, solvate, prodrug, stereoisomer, or tautomer thereof)) for use in the manufacture of a medicament for treating and/or preventing a disease and/or disorder in which a farnesoid X receptor (FXR) plays a role. In some embodiments, a FXR plays a role in a disease and/or disorder in that the FXR is involved in a pathway, mechanism, or action associated with the disease and/or disorder such as, e.g., in the control of enterohepatic circulation of bile acids, bile acid synthesis, and/or secretion and bile acid uptake into hepatocytes.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWING

FIG. 1 shows a MS/MS spectra of the metabolites of the compound of Example 4.

DETAILED DESCRIPTION OF EXAMPLE EMBODIMENTS

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein. A "farnesoid X receptor" or "FXR" as used herein is a farnesoid X receptor from any source and/or that is present in a subject and/or expressed in any form. In some embodiments, a farnesoid X receptor is from and/or is present and/or expressed in an animal such as, e.g., a mammal. In some embodiments, a farnesoid X receptor is from and/or is present and/or expressed in a primate, cow, sheep, goat, horse, dog, cat, rabbit, rat, mouse, fish, bird, and/or the like. In some embodiments, a farnesoid X receptor is from and/or is present and/or expressed in a human.

The terms "modulate" and "modulating", in reference to a FXR, refer to the ability of a compound (e.g., a compound of the present invention) to activate or inhibit one or more function(s), action(s), and/or characteristic(s) of the FXR, either directly or indirectly. This may occur in vitro or in vivo and is intended to encompass antagonism, agonism, partial antagonism and/or partial agonism of a function, action, and/or characteristic associated with a FXR.

The term "activating", in reference to a FXR, refers to the ability of a compound (e.g., a compound of the present invention) to activate, increase or enhance a function, action, and/or characteristic associated with the FXR, and, thus, the compound is an FXR agonist.

The term "modulator", in reference to a FXR, refers to a compound (e.g., a compound of the present invention) that modulates a FXR. In some embodiments, a compound of the present invention modulates a FXR by activating one or more function(s), action(s), and/or characteristic(s) of the FXR.

The term "agonist" refers to a compound (e.g., a compound of the present invention) that combines with and/or binds to a specific receptor (e.g., a FXR) and activates, increases or enhances a function, action, and/or characteristic associated with the receptor. The term "agonist" includes both a full agonist and a partial agonist, which activates, increases or enhances a function, action, and/or characteristic associated with the receptor (e.g., FXR) to a lesser extent than a full agonist and/or has partial efficacy at the receptor compared to a full agonist. In some embodiments, a compound of the present invention is an FXR agonist. In some embodiments, a compound of the present invention is an agonist and activates a FXR providing the same or substantially the same reaction and/or pharmacological response typically produced by the binding of an endogenous agonist.

"Substantially the same" as used herein in reference to a measurable value and/or response means being within about ±10% of the compared to value and/or response.

The term "$C_{1-3}$ alkyl" means a saturated or unsaturated alkyl chain having 1 to 3 carbon atoms which may be a straight chain or branched chain. Examples thereof include, but are not limited to, methyl, ethyl, propyl and isopropyl.

The term "$C_{1-6}$ alkyl" means a saturated or unsaturated alkyl chain having 1 to 6 carbon atoms which may be a straight chain or branched chain. Examples thereof include, but are not limited to, methyl, ethyl, propyl, isopropyl, n-butyl, isobutyl, tert-butyl, n-pentyl, isopentyl, neopentyl and hexyl.

The term "$C_{1-3}$ alkoxy" means a straight or branched chain saturated or unsaturated hydrocarbon containing 1-3 carbon atoms containing a terminal oxygen in the chain and the straight or branched chain saturated or unsaturated hydrocarbon is attached to a parent or principal compound through the oxygen. Examples thereof include, but are not limited to, methoxy, ethoxy and propoxy.

The term "$C_{1-6}$ alkoxy" means a straight or branched chain saturated or unsaturated hydrocarbon containing 1-6 carbon atoms containing a terminal oxygen in the chain and the straight or branched chain saturated or unsaturated hydrocarbon is attached to a parent or principal compound through the oxygen. Examples thereof include, but are not limited to, methoxy, ethoxy propoxy, butoxy, t-butoxy, and pentoxy.

The terms "halo$C_{1-3}$ alkyl" and "halo$C_{1-6}$ alkyl" mean that one or more hydrogen atom(s) in the alkyl chain of the $C_{1-3}$ alkyl and $C_{1-6}$ alkyl, respectively, are replaced by a halogen atom. Examples thereof include, but are not limited to, difluoromethyl and trifluoromethyl.

The term "halo$C_{1-6}$ alkoxy" means that one or more hydrogen atom(s) in the hydrocarbon chain of the $C_{1-6}$ alkoxy is replaced by a halogen atom.

The term "$C_{3-6}$ cycloalkyl" means a saturated or unsaturated (e.g., partially or fully unsaturated) mono- or bicyclic ring system comprising 3 to 6 carbon atoms. Examples thereof include, but are not limited to, cyclopropyl, cyclobutyl, cyclopentyl and cyclohexyl.

The term "$C_{3-10}$ cycloalkyl" means a saturated or unsaturated (e.g., partially or fully unsaturated) mono-, bi-, Spiro- or multicyclic ring system comprising 3 to 10 carbon atoms. Examples thereof include, but are not limited to, cyclopropyl, cyclobutyl, cyclopentyl, cyclohexyl, cycloheptyl, cyclooctyl, cyclononane, cyclodecane, bicyclo[3.2.0]heptane, bicyclo[3.3.0]octane, bicyclo[4.3.0]nonane, spiro[2.3]hexane, spiro[2.5]octane, spiro[3.4]octane, spiro[4.5]decane and spiro[5.5]decane.

The term "5-10 membered monocyclic or bicyclic heteroaryl containing 1-2 heteroatoms" means a monocyclic or bicyclic heteroaromatic ring that contains 5-10 atoms selected from carbon, nitrogen, oxygen, and/or sulfur with 1-2 of those atoms being a heteroatom (i.e., nitrogen, oxygen, and/or sulfur). For such a bicyclic heteroaromatic ring system, the heteroatom(s) may be present in one or both rings including any bridgehead atoms. Examples of 5-10 membered monocyclic heteroaryls containing 1-2 heteroatoms include, but are not limited to, pyrrolyl, imidazolyl, furanyl, thiophenyl, pyridinyl, pyrimidinyl, pyrazinyl, pyrazolyl, oxazolyl and isoxazolyl. Examples of 5-10 membered bicyclic heteroaryls containing 1-2 heteroatoms include, but are not limited to, quinolinyl, isoquinolinyl, quinoxalinyl, benzimidazolyl, benzisoxazolyl, benzofuranyl, benzoxazolyl, indolyl and indolizinyl. The nitrogen or sulphur atom of a 5-10 membered monocyclic or bicyclic heteroaryl containing 1-2 heteroatoms may also be optionally oxidized to the corresponding N-oxide, S-oxide or S,S-dioxide. If not stated otherwise, a 5-10 membered monocyclic or bicyclic heteroaryl system as described herein can be connected via a carbon or nitrogen atom.

The term "4 or 5 membered monocyclic heterocycle or heteroaryl containing 1-3 heteroatoms from N, O and S" means a monocyclic ring that contains 4 or 5 atoms selected from carbon, nitrogen, oxygen and/or sulfur with 1-3 of those atoms being nitrogen, oxygen and/or sulfur. A heterocycle group can be saturated or unsaturated (e.g., fully or partially unsaturated) and a heteroaryl group is unsaturated and aromatic. Examples of 4 or 5 membered monocyclic heterocycles containing 1-3 heteroatoms selected from N, O, and S include, but are not limited to, oxetane, tetrahydrofuran, pryrrolidine, isoxazoline, oxazolidinone, and γ-lactam. Further examples of 4 or 5 membered monocyclic heterocycles containing 1-3 heteroatoms selected from N, O, and S include, but are not limited to, pyrazole, imidazole, triazole, isoxazole, and oxadiazole.

The term "N-oxide" denotes a compound where the nitrogen in the heteroaromatic system (e.g., pyridinyl) is oxidized. Such compounds can be obtained by reacting a compound of the present invention (such as including a pyridinyl) with $H_2O_2$ or a peracid in an inert solvent.

"Halogen" refers to fluorine, chlorine, bromine and iodine. In some embodiments, the halogen is fluorine or chlorine.

The term "optionally substituted" is understood to mean that a given chemical moiety (e.g., an alkyl group) can (but is not required to) be bonded to other substituents (e.g., heteroatoms). For instance, an alkyl group that is optionally substituted can be a fully saturated alkyl chain (e.g., a pure hydrocarbon). Alternatively, the same optionally substituted alkyl group can have one or more substituent(s) different from hydrogen. For instance, it can, at any point along the chain, be bound to a halogen atom, a hydroxyl group, or any other substituent described herein. Thus, the term "optionally substituted" means that a given chemical moiety has the potential to contain other functional groups, but does not necessarily have any further functional groups.

The term "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

The term "pharmaceutically acceptable salt" refers to a salt of a compound which is, within the scope of sound medical judgment, suitable for use in contact with the tissues of humans and lower animals without undue toxicity, irritation, allergic response and the like, and is commensurate with a reasonable benefit/risk ratio. Pharmaceutically acceptable salts are well known in the art.

For a detailed review of pharmaceutically acceptable salts see J. Pharmaceutical Sciences, 66: 1-19 (1977), by Berge et al. In some embodiments, the salts can be prepared in situ during the final isolation and/or purification for a compound of the invention, or separately by reaction of the free acid function with a suitable inorganic or organic base. Suitable salts include, but are not limited to, metals, such as sodium, potassium and calcium, or amines, such as triethylammonium, ethanolammonium and lysine.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "prodrug" refers to a prodrug of a compound which is, within the scope of sound medical judgment, suitable for use in contact with the tissues of humans and lower animals with undue toxicity, irritation, allergic response, and/or the like, commensurate with a reasonable benefit/risk ratio, and effective for their intended use, as well as the zwitterionic forms, where possible, of a compound of the present invention. "Prodrug", as used herein means a compound that is convertible in vivo by metabolic means (e.g., by hydrolysis) to afford a compound of the present invention (e.g., a compound of Formula I). Various forms of prodrugs are known in the art, for example, as discussed in Bundgaard, (ed.), Design of Prodrugs, Elsevier (1985); Widder, et al. (ed.), Methods in Enzymology, Vol. 4, Academic Press (1985); Krogsgaard-Larsen, et al., (ed). "Design and Application of Prodrugs, Textbook of Drug Design and Development", Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "amino acid conjugate" refers to a conjugate of a compound of the present invention (e.g., a compound of Formula I) with an amino acid. Preferably, such amino acid conjugates of the present invention will have the added advantage of enhanced integrity in bile and/or intestinal fluids. Suitable amino acids include, but are not limited to, glycine and taurine. Thus, the present invention encompasses the glycine and taurine conjugates of a compound of Formula I.

The term "GW4064" is an FXR agonist compound having the following structure:

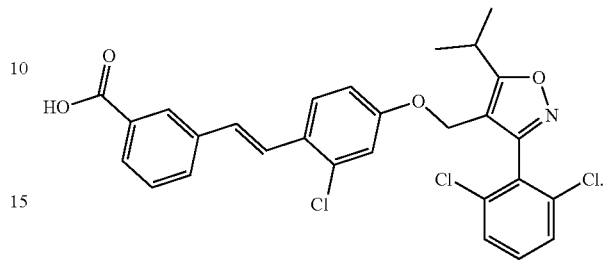

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$alkoxy)$C_{1-3}$alkyl," is attached to the rest of the molecule at the alkyl end. Further examples include methoxyethyl, where the point of attachment is at the ethyl end, and methylamino, where the point of attachment is at the amine end.

Unless indicated otherwise, where a mono or bivalent group is described by its chemical formula, including one or two terminal bond moieties indicated by "-," it will be understood that the attachment is read from left to right.

Unless otherwise stated, structures depicted herein are meant to include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Provided according to embodiments of the present invention are compounds having a structure represented by Formula I:

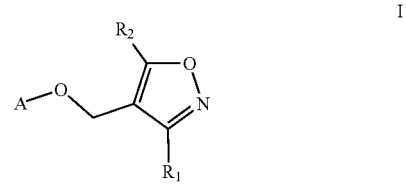

wherein:
$R_1$ is a $C_{3-10}$ cycloalkyl, phenyl or pyridyl, each of which is optionally substituted with 1-3 $R_{1a}$;
each $R_{1a}$ is independently selected from the group consisting of a halogen, $C_{1-6}$ alkyl, halo$C_{1-6}$ alkyl, $C_{1-6}$ alkoxy, halo$C_{1-6}$ alkoxy and cyclopropyl;
$R_2$ is a $C_{1-3}$ alkyl, halo$C_{1-3}$ alkyl or cyclopropyl, each of which is optionally substituted with a $C_{1-3}$ alkyl or halo$C_{1-3}$ alkyl;

A is selected from:

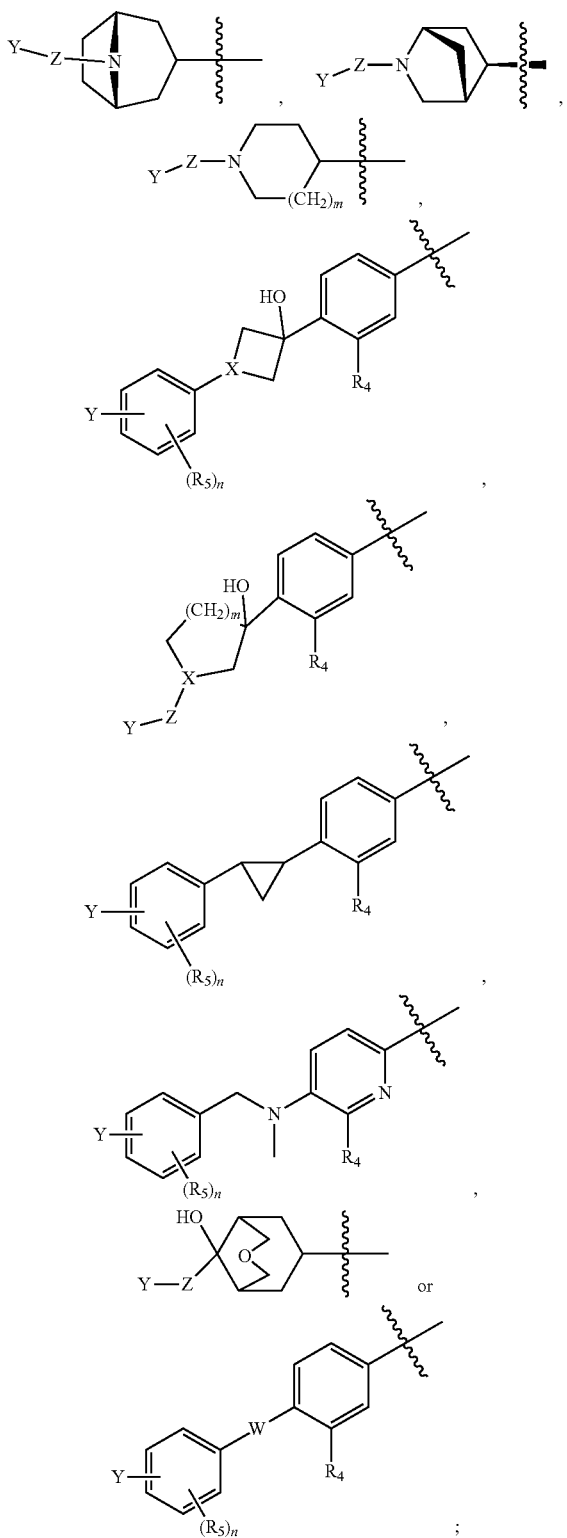

Y is —S(O)OH or —S(O)$_2$OH, optionally wherein Y is —S(O)OH;

Z is phenyl or a 5-10 membered monocyclic or bicyclic heteroaryl containing 1-2 heteroatoms selected from N, O and S, wherein the phenyl or 5-10 membered monocyclic or bicyclic heteroaryl is optionally substituted with 1-2 R$_6$;

W is a 4 or 5 membered monocyclic heterocycle or heteroaryl containing 1-3 heteroatoms from N, O and S;

each R$_6$ is independently selected from the group consisting of a halogen, C$_{1-6}$ alkyl, haloC$_{1-6}$ alkyl, C$_{1-6}$ alkoxy, haloC$_{1-6}$ alkoxy, and cyclopropyl;

X is N or CH;

R$_4$ is a H, C$_{1-6}$ alkyl, C$_{1-6}$ alkoxy, haloC$_{1-6}$ alkyl, C$_{3-6}$ cycloalkyl, or halogen;

each R$_5$ is independently selected from the group consisting of a C$_{1-6}$ alkyl, C$_{3-6}$ cycloalkyl, haloC$_{1-6}$ alkyl, C$_{1-6}$ alkoxy, haloC$_{1-6}$ alkoxy and halogen;

m is an integer of 0, 1 or 2; and n is an integer of 0, 1, 2 or 3; or an enantiomer, stereoisomer, tautomer, solvate, hydrate, prodrug, amino acid conjugate, metabolite, or pharmaceutically acceptable salt thereof.

In some embodiments, a compound of the present invention is a metabolite (i.e. having undergone metabolism or biotransformation in the subject). In some embodiments, a compound of the present invention is a sulfinic acid (or its corresponding sulfinate salt) compound or a sulfonic acid (or its corresponding sulfonate salt) compound. In some embodiments, a compound of the present invention may be a sulfinic acid metabolite, which may be a corresponding sulfonic acid of the compound (e.g., a compound having a —S(O)$_2$OH or —S(O)$_2$O$^-$ group replacing a —S(O)OH or —S(O)O$^-$ group in the compound) or a corresponding sulfinate ester of the compound (e.g., a compound having a —S(O)O(C$_{1-6}$ alkyl) group replacing a —S(O)OH or —S(O)O$^-$ group in the compound). In some embodiments, a compound of the present invention is a sodium salt. In some embodiments, a compound of the present invention is a sulfinate salt (e.g. a sodium sulfinate salt).

In some embodiments, a compound of the present invention may have a different metabolic profile compared to a corresponding carboxylic acid compound (i.e., a compound having a —COOH or —COO$^-$ group replacing a —S(O)OH or —S(O)O$^-$ group in the compound). In some embodiments, a compound of the present invention may have beneficial liver safety effects and/or improved liver safety compared to another compound such as, e.g., a corresponding carboxylic acid compound.

In some embodiments, a compound of the present invention may be more efficacious than, be less toxic than, be longer acting than, be more potent than, produce fewer side effects than, be more easily absorbed than, have a better pharmacokinetic profile (e.g., higher oral bioavailability and/or lower clearance) than, and/or have other useful pharmacological, physical or chemical properties than a compound known in the prior art. Such effects may be evaluated clinically, objectively and/or subjectively by a health care professional, a treatment subject or an observer.

In some embodiments, in a compound of Formula I, A is selected from:

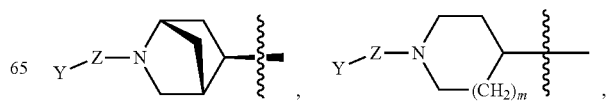

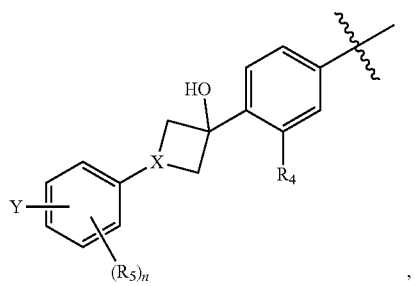
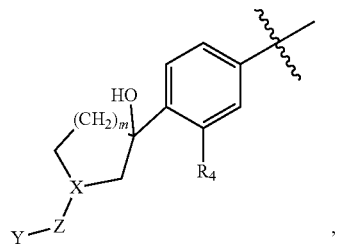
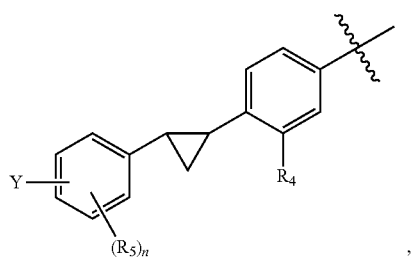
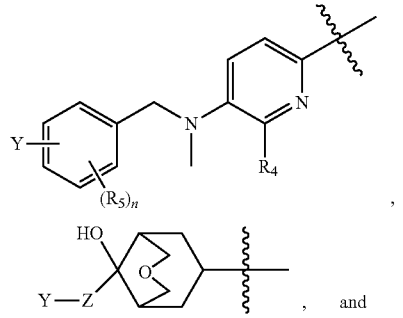
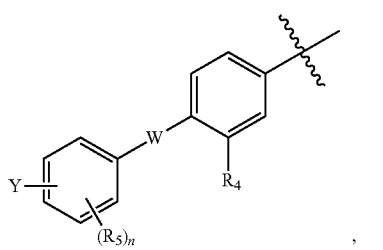
wherein Z, X, W, R₄, R₅ and n are each as defined above.
In some embodiments, in a compound of Formula I, A is selected from:
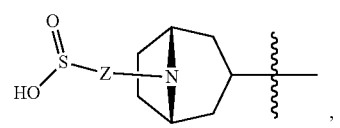
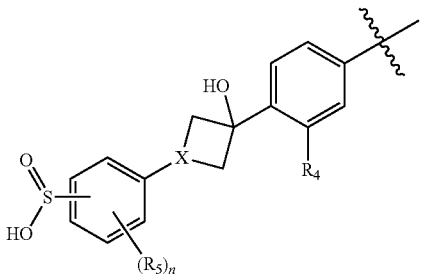
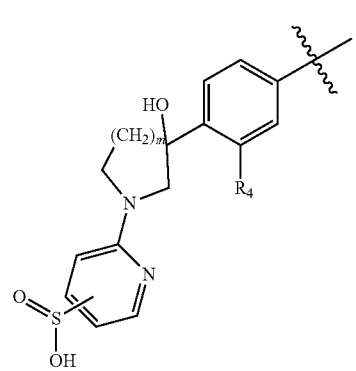
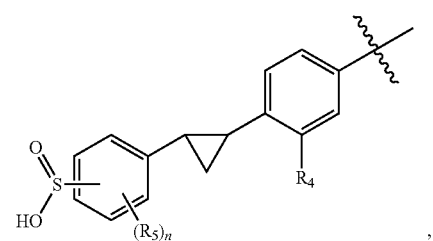
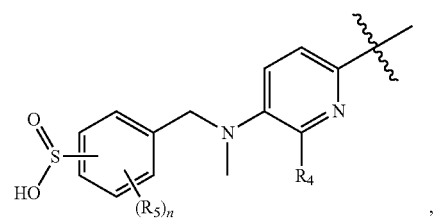
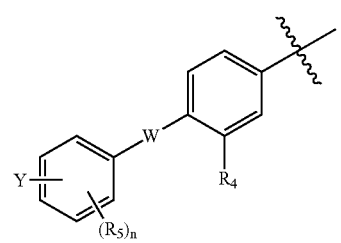
wherein Z, X, W, R₄, R₅ and n are each as defined above.
Also provided according to embodiments of the present invention are compounds having a structure represented Formula II, III, IV, V, VI, VII, VIII, IX and X:

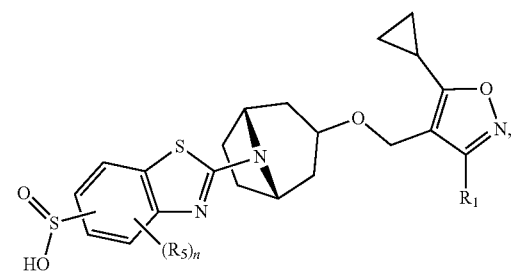

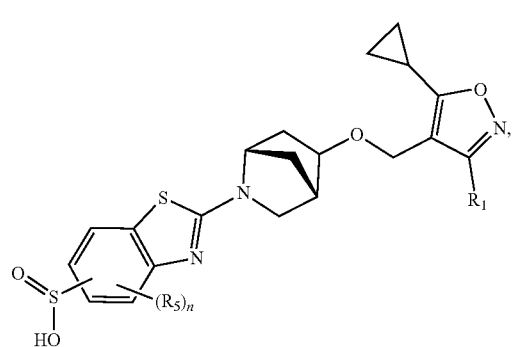

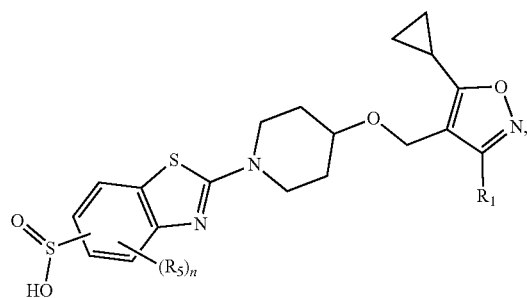

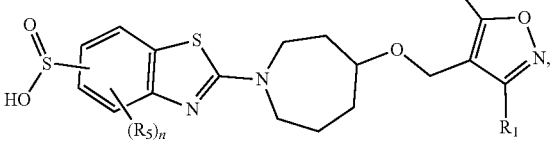

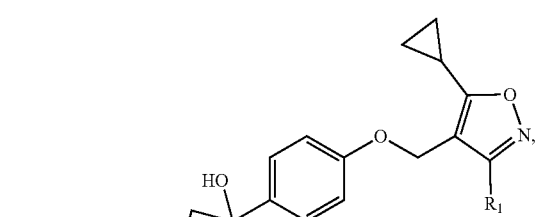

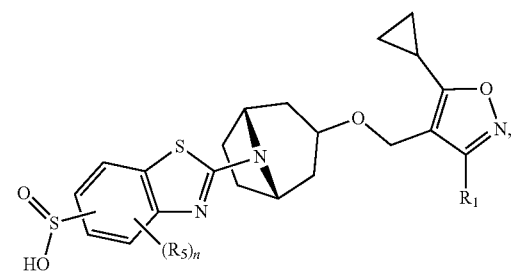

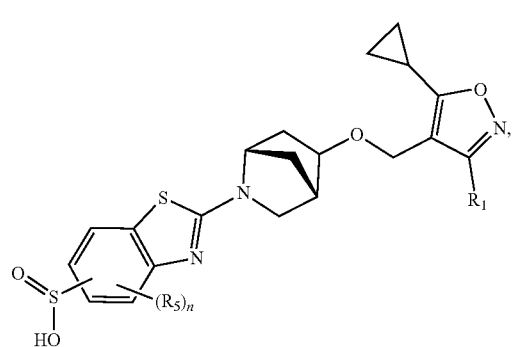

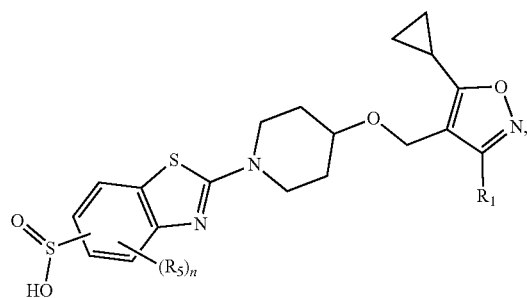

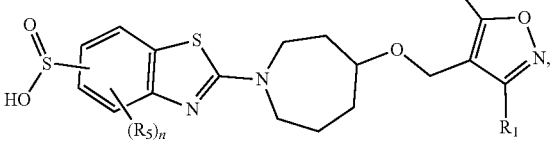

wherein $R_1$, $R_5$ and n are each as defined above; or an enantiomer, stereoisomer, tautomer, solvate, hydrate, prodrug, amino acid conjugate, metabolite, or pharmaceutically acceptable salt thereof.

In some embodiments, $R_1$ for a compound of the present invention (e.g., a compound of Formula I, II, III, IV, V, VI, VII, VIII, IX or X) is phenyl that is optionally substituted with 1-3 $R_{1a}$, wherein each $R_{1a}$ is independently selected from the group consisting of a halogen, $C_{1-6}$ alkyl, halo$C_{1-6}$ alkyl, $C_{1-6}$ alkoxy, and halo$C_{1-6}$ alkoxy. In some embodiments, $R_1$ for a compound of the present invention is phenyl that is optionally substituted with 1-3 $R_{1a}$, wherein each $R_{1a}$ is independently selected from the group consisting of a halogen, methoxy, methyl, trifluoromethyl, trifluoromethoxy, and difluoromethoxy. In some embodiments, $R_1$ for a compound of the present invention is phenyl. Y for a compound of the present invention is directly bound to Z via a carbon or heteroatom in the phenyl ring or in the 5-10 membered monocyclic or bicyclic heteroaryl ring, thereby providing a sulfur-carbon or sulfur-heteroatom bond.

According to some embodiments, provided is a compound having a structure represented by Formula IIa:

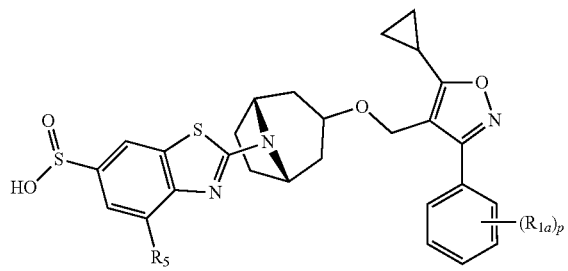

wherein:
each $R_{1a}$ is independently selected from the group consisting of a halogen, trifluoromethyl, trifluoromethoxy and difluoromethoxy;
$R_5$ is methyl, methoxy, fluoro or trifluoromethoxy;
p is an integer of 0 or 1; or
an enantiomer, stereoisomer, tautomer, solvate, hydrate, prodrug, amino acid conjugate, metabolite, or pharmaceutically acceptable salt thereof.

Some embodiments of the present invention provide a compound selected from: sodium 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-sulfinate, sodium 2-((1R,3r,5 S)-3-((5-cyclopropyl-3-(2-(trifluoromethoxy)phenyl)isoxazol-4-yl)methoxy)-8-azabicyclo [3.2.1]octan-8-yl)-4-methylbenzo[d]thiazole-6-sulfinate, sodium 3-(3-(2-chloro-4-((5-cyclopropyl-3-(2,6-dichlorophenyl)isoxazol-4-yl)methoxy)phenyl)-3-hydroxyazetidin-1-yl)benzenesulfinate, sodium 4-(3-(2-chloro-4-((5-cyclopropyl-3-(2,6-dichlorophenyl)isoxazol-4-yl)methoxy)phenyl)-3-hydroxycyclobutyl)benzenesulfinic acid, and/or sodium 4-(2-(2-chloro-4-((5-cyclopropyl-3-(2,6-dichlorophenyl)isoxazol-4-yl)methoxy)phenyl) cyclopropyl)benzenesulfinate.

Provided according to some embodiments of the present invention is a composition (e.g., a pharmaceutical composition) comprising a compound of the present invention (e.g., a compound of Formula I, II, III, IV, V, VI, VII, VIII, IX or X). In some embodiments, a pharmaceutical composition of the present invention comprises a compound of the present invention and a pharmaceutically acceptable carrier.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient (e.g., a compound of the present invention), its use in the therapeutic and/or pharmaceutical compositions is contemplated.

Compounds of the invention are indicated as pharmaceuticals. According to a further aspect of the invention there is provided a compound of the invention, for use as a pharmaceutical (e.g. for use in medicine).

According to some embodiments, a compound and/or composition of the present invention is administered to a subject. In some embodiments, a method of modulating a farnesoid X receptor (FXR) in a subject is provided, the method comprising administering to the subject a compound of the present invention and/or a composition of the present invention. In some embodiments, a method of activating a farnesoid X receptor (FXR) is provided, the method comprising administering to a subject a compound of the present invention and/or a composition of the present invention.

In some embodiments, a method of treating and/or preventing a disease or disorder in which a farnesoid X receptor (FXR) plays a role is provided, the method comprising administering to a subject in need thereof an effective amount (e.g., a therapeutically effective amount, a treatment effective amount, and/or a prevention effective amount) of a compound of the present invention and/or a composition of the present invention. In some embodiments, the disease or disorder is a bile acid related disorder, metabolic syndrome, type-2 diabetes, diabetic nephropathy, hyperlipidemia, hypertriglyceridemia, obesity, liver cirrhosis, primary biliary cirrhosis (PBC), primary sclerosing cholangitis (PSC), fatty liver disease, nonalcoholic steatohepatitis (NASH), non-alcoholic fatty liver disease (NAFLD), alcoholic liver disease, chemotherapy associated steatohepatitis (CASH), hepatitis B, inflammatory autoimmune diseases, inflammatory bowel disease, Crohn's disease, ulcerative colitis, proctitis, pouchitis, Celiac's Disease, bile acid diarrhea, multiple sclerosis, atherosclerosis, kidney disorders (including chronic kidney disease) or cancer (e.g., a hepatic cancer, colon cancer or breast cancer).

The term "therapeutically effective amount" refers to an amount of a compound of the present invention (e.g., a compound of Formula I, II, III, IV, V, VI, VII, VIII, IX or X) that is sufficient to achieve or elicit a therapeutically useful response or a stated effect in a subject. Accordingly, a therapeutically effective amount of a compound of Formula I used for the treatment of a condition mediated by a FXR can be an amount sufficient for the treatment of the condition mediated by the FXR As used herein, the term "subject" refers to an animal. Typically, the animal is a mammal. A subject also refers to, for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

The terms "treat", "treating", "treatment of" and grammatical variations thereof in reference to a disease, or condition refer to any type of treatment that imparts a benefit to a subject and may mean that the severity of the subject's condition is reduced, at least partially improved or ameliorated and/or that some alleviation, mitigation or decrease in at least one clinical symptom associated with a disease, disorder, or condition is achieved and/or there is a delay in the progression of the symptom. In some embodiments, the severity of a symptom associated with a disease, disorder, or condition mediated by a FXR may be reduced in a subject compared to the severity of the symptom in the absence of a method of the present invention. In some embodiments, "treat", "treating", "treatment of" and grammatical variations thereof in reference to a disease or disorder refer to ameliorating the disease or disorder (i.e., slowing or arresting or reducing the development of the disease or disorder or at least one clinical symptom thereof). In some embodiments, "treat", "treating" or "treatment of" and grammatical variations thereof in reference to a disease or disorder refer to alleviating or ameliorating at least one physical parameter including those which may not be discernible by the subject. In some embodiments, "treat", "treating" or "treatment of" and grammatical variations thereof in reference to a disease or disorder refer to modulating the disease or disorder, either physically (e.g., stabilization of a discernible symptom), physiologically (e.g., stabilization of a physical parameter), or both.

In some embodiments, a compound of the present invention may be administered to a subject in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering a composition of the present invention.

The terms "prevent," "preventing" and "prevention" (and grammatical variations thereof) refer to avoidance, reduction and/or delay of the onset of a symptom associated with a disease or disorder (e.g., a disease, disorder, or condition mediated by a FXR) and/or a reduction in the severity of the onset of symptom associated with a disease or disorder (e.g., a disease, disorder, or condition mediated by a FXR) relative to what would occur in the absence of a method of the present invention. The prevention can be complete, e.g., the total absence of the symptom. The prevention can also be partial, such that the occurrence of the symptom in the subject and/or the severity of onset is less than what would occur in the absence of a method of the present invention.

In some embodiments, a compound of the present invention may be administered in a prevention effective amount. A "prevention effective" amount as used herein is an amount that is sufficient to prevent (as defined herein) a symptom associated with a disease or disorder (e.g., a disease, disorder, or condition mediated by a FXR) in a subject. Those skilled in the art will appreciate that the level of prevention need not be complete, as long as some benefit is provided to the subject. In some embodiments, a prevention effective amount may be achieved by administering a composition of the present invention.

The terms "administer", "administering", "administration" and grammatical variations thereof as used herein refer to directly administering to a subject a compound of the present invention (or a pharmaceutically acceptable salt, etc., thereof) and/or a composition of the present invention. In some embodiments, a compound and/or composition of the present invention is administered to the subject in an amount that can form an equivalent amount of the active compound within the subject's body.

A compound of the present invention can be administered in a therapeutically effective amount to treat and/or prevent a disease or disorder and/or to prevent the development thereof in a subject. Administration of a compound of the present invention can be accomplished via any mode of administration for therapeutic agents such as, for example oral, rectal, topical, and/or parenteral administration may be employed. In some embodiments, a compound of the present invention is administered orally.

Depending on the intended mode of administration, a compound of the present invention and/or composition of the present invention can be in a dosage form known to those skilled in the pharmaceutical practices, such as, for example, injectables, tablets, suppositories, pills, time-release capsules, emulsions, syrups, powders, liquids, suspensions, and/or the like.

Typical pharmaceutical compositions include, but are not limited to, tablets, pills, powders or gelatin capsules comprising the active ingredient (e.g., a compound of the present invention) and a pharmaceutically acceptable carrier such as for example:

a) a diluent, e.g., purified water, corn oil, olive oil, sunflower oil, fish oils, such as EPA or DHA or their esters or triglycerides or mixtures thereof, lactose, dextrose, sucrose, mannitol, sorbitol, cellulose and/or glycine:

b) a lubricant, e.g., silica, talcum, stearic acid its magnesium or calcium salt and/or polyethylene glycol; for tablets also;

c) a binder, e.g., magnesium aluminum silicate, starch paste, gelatin, tragacanth, methylcellulose, sodium carboxymethylcellulose, natural and synthetic gums such as acacia tragacanth or sodium alginate, waxes and/or polyvinylpyrrolidone, if desired;

d) a disintegrant, e.g., starches, agar, algic acid or its sodium salt, and/or effervescent mixtures;

e) absorbent, colorant, flavorant and/or sweetener;

f) an emulsifier or dispersing agent, e.g. Labrasol, HPMC, labrafil, peceol, capmul, vitamin E TGPS and/or other acceptable emulsifier; and/or g) an agent that enhances absorption of the compound such as cyclodextrin, hydroxypropyl-cyclodextrin, PEG400, and/or PEG200.

Liquid, particularly injectable, compositions can, for example, be prepared by dissolution, dispersion, etc. For example, a compound of the present invention is dissolved in or mixed with a pharmaceutically acceptable solvent such as, for example, water, saline, aqueous dextrose, glycerol, ethanol, and/or the like, to thereby form an injectable isotonic solution or suspension. Said composition may be sterilized and/or contain adjuvants, such as preserving, stabilizing wetting or emulsifying agents, solution promoters, salts for regulating osmotic pressure and/or buffers.

A compound of the present invention may also be formulated as a suppository that can be prepared from fatty emulsions or suspensions; using polyalkylene glycols such as propylene glycol, as the carrier.

A compound of the present invention may also be delivered by the use of monoclonal antibodies as individual carriers to which the compound is coupled. A compound of the present invention may be coupled with a soluble polymer as a targetable drug carrier. Such polymers can include, but are not limited to, polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, a compound of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphiphillic block copolymers of hydrogels. In one embodiment disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection. In addition, they may also contain other therapeutically valuable substances. Said compositions may be prepared according to conventional mixing, granulating and/or coating methods, respectively, and contain about 0.1-75%, or contain about 1-50%, of the active ingredient.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc, zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing a compound of the present invention in the proper medium. Absorption enhancers can also be used to increase the flux of the compound across the skin. The rate can be controlled by either providing a rate controlling membrane or by dispersing the compound in a polymer matrix or gel.

Compositions of the present invention can be prepared according to conventional mixing, granulating and/or coating methods, respectively, and the present pharmaceutical compositions can contain from about 0.1% to about 99% of compound by weight or volume.

The present invention further provides pharmaceutical compositions and dosage forms that comprise one or more agents that reduce the rate by which a compound of the present invention as an active ingredient will decompose. Such agents, which are referred to herein as "stabilizers" include, but are not limited to, antioxidants such as ascorbic acid, pH buffers, and/or salt buffers, etc.

The dosage regimen utilizing a compound of the present invention may be selected in accordance with a variety of factors including type, species, age, weight, sex and/or medical condition of the subject; the severity of the condition to be treated; the route of administration; the renal or hepatic function of the subject; and the particular disclosed compound employed. A physician, clinician or veterinarian of ordinary skill can readily determine the effective amount of each of the active ingredients necessary to prevent, treat or inhibit the progress of the disorder or disease.

Effective dosage amounts of a compound of the present invention, when used for the indicated effects, range from about 0.5 mg to about 5000 mg of the compound as needed to treat the condition.

A compound of the present invention may be administered either simultaneously with, or before or after, one or more other therapeutic agent(s). A compound of the present invention may be administered separately, by the same or different route of administration, or together in the same pharmaceutical composition as the other therapeutic agent(s).

In some embodiments, the invention provides a product comprising a compound of Formula I and at least one other therapeutic agent as a combined preparation for simultaneous, separate or sequential use in therapy. In some embodiments, the one or more additional therapeutic agent(s) are an ACE inhibitor, acetyl CoA carboxylase inhibitor, adenosine A3 receptor agonist, adiponectin receptor agonist, AKT protein kinase inhibitor, AMP-activated protein kinases (AMPK), amylin receptor agonist, angiotensin II AT-1 receptor antagonist, autotaxin inhibitors, bioactive lipid, calcitonin agonist, caspase inhibitor, caspase-3 stimulator, cathepsin inhibitor, caveolin 1 inhibitor, CCR2 chemokine antagonist, CCR3 chemokine antagonist, CCR5 chemokine antagonist, chloride channel stimulator, CNR1 inhibitor, cyclin D1 inhibitor, cytochrome P450 7A1 inhibitor, DGAT1/2 inhibitor, dipeptidyl peptidase IV inhibitor, endosialin modulator, eotaxin ligand inhibitor, extracellular matrix protein modulator, farnesoid X receptor agonist, fatty acid synthase inhibitors, FGF1 receptor agonist, fibroblast growth factor (FGF-15, FGF-19, FGF-21) ligands, galectin-3 inhibitor, glucagon receptor agonist, glucagon-like peptide 1 agonist, G-protein coupled bile acid receptor 1 agonist, hedgehog (Hh) modulator, hepatitis C virus NS3 protease inhibitor, hepatocyte nuclear factor 4 alpha modulator (HNF4A), hepatocyte growth factor modulator, HMG CoA reductase inhibitor, IL-10 agonist, IL-17 antagonist, ileal sodium bile acid cotransporter inhibitor, insulin sensitizer, integrin modulator, intereukin-1 receptor-associated kinase 4 (IRAK4) inhibitor, Jak2 tyrosine kinase inhibitor, klotho beta stimulator, 5-lipoxygenase inhibitor, lipoprotein lipase inhibitor, liver X receptor, LPL gene stimulator, lysophosphatidate-1 receptor antagonist, lysyl oxidase homolog 2 inhibitor, matrix metalloproteinases (MMPs) inhibitor, MEKK-5 protein kinase inhibitor, membrane copper amine oxidase (VAP-1) inhibitor, methionine aminopeptidase-2 inhibitor, methyl CpG binding protein 2 modulator, microRNA-21(miR-21) inhibitor, mitochondrial uncoupler, myelin basic protein stimulator, NACHT LRR PYD domain protein 3 (NLRP3) inhibitor, NAD-dependent deacetylase sirtuin stimulator, NADPH oxidase inhibitor (NOX), nicotinic acid receptor 1 agonist, P2Y13 purinoceptor stimulator, PDE 3 inhibitor, PDE 4 inhibitor, PDE 5 inhibitor, PDGF receptor beta modulator, phospholipase C inhibitor, PPAR alpha agonist, PPAR delta agonist, PPAR gamma agonist, PPAR gamma modulator, protease-activated receptor-2 antagonist, protein kinase modulator, Rho associated protein kinase inhibitor, sodium glucose transporter-2 inhibitor, SREBP transcription factor inhibitor, STAT-1 inhibitor, stearoyl CoA desaturase-1 inhibitor, suppressor of cytokine signalling-1 stimulator, suppressor of cytokine signalling-3 stimulator, transforming growth factor 3 (TGF-β3), transforming growth factor β activated Kinase 1 (TAKi), thyroid hormone receptor beta agonist, TLR-4 antagonist, transglutaminase inhibitor, tyrosine kinase receptor modulator, GPCR modulator, nuclear hormone receptor modulator, WNT modulators, and/or YAP/TAZ modulator.

In some embodiments, the therapy is the treatment or prevention of a disease or condition mediated by a FXR. Products provided as a combined preparation include, but are not limited to, a composition comprising a compound of Formula I and one or more therapeutic agent(s) together in the same pharmaceutical composition, or the compound of Formula I and one or more therapeutic agent(s) in a separate form, e.g. in the form of a kit.

In some embodiments, a compound of the present invention is an isotopically labelled compound. An "isotopically labelled compound" as used herein refers to a compound in which at least one atomic position is enriched in a specific isotope of the designated element to a level which is significantly greater than the natural abundance of that isotope. For example, one or more hydrogen atom positions in a compound can be enriched with deuterium to a level that is significantly greater than the natural abundance of deuterium, for example, enrichment to a level of at least 1%, preferably at least 20% or at least 50%. Such a deuterated compound may, for example, be metabolized more slowly than its non-deuterated analogue, and therefore exhibit a longer half-life when administered to a subject (Annual Reports In Medicinal Chemistry, Vol. 26, 2011, Chapter 24—Deuterium in Drug Discovery and Development, pages 403-417). Such compounds can be synthesized using methods known in the art, for example, by employing deuterated starting materials. Unless stated to the contrary, isotopically labelled compounds are pharmaceutically acceptable.

The present invention is explained in greater detail in the following non-limiting examples.

EXAMPLES

The reaction schemes described below are intended to provide a general description of the methodology employed in the preparation of the compounds of the present invention. The examples provided herein are offered to illustrate but not limit the compounds of the present invention, as well as the preparation of such compounds and intermediates All starting materials, building blocks, reagents, acids, bases, dehydrating agents, solvents and catalysts utilized to synthesize the compounds of the present invention are either commercially available or can be routinely prepared by procedures described in the literature, for example, Houben-Weyl "Science of Synthesis" volumes 1-48, Georg Thieme Verlag, and subsequent versions thereof.

A reaction may be carried out in the presence of a suitable solvent or diluent or of mixture thereof in a manner known to those skilled in the art of organic synthesis. A reaction may also be carried out, if needed, in the presence of an acid or a base, with cooling or heating, for example in a temperature range from about −30° C. to about 150° C. In some embodiments, a reaction is carried out in a temperature range from about 0° C. to about 100° C., and more particularly, in a temperature range from room temperature to about 80° C., in an open or closed reaction vessel and/or in the atmosphere of an inert gas, for example nitrogen.

ABBREVIATIONS aq. Aqueous
AMP adenosine monophosphate
ATP adenosine triphosphate
Boc tertiary butyl carboxy
br broad
n-BuLi n-butyl lithium
cDNA complementary deoxyribonucleic acid
$CO_2$ carbon dioxide
Cu(I)I copper (I) iodide
d doublet
dd doublet of doublets
DIBAL-H diisobutylaluminium hydride
DMF dimethylfomamide
DMSO dimethylsulfoxide
$Et_3N$ triethylamine
EtOAc ethyl acetate
EtOH ethanol
g gramme
h hour(s)
LCMS liquid chromatography and mass spectrometry
m multiplet
M molar
MeOH methanol
$MgSO_4$ magnesium sulfate
MS mass spectrometry
N Normal
$NaHCO_3$ sodium hydrogencarbonate
NaOH sodium hydroxide
NaOMe sodium methoxide
m multiplet
mg milligram
min(s) minute(s)
ml milliliter
m mol
mmol millimol
$Na_2SO_4$ sodium sulfate
NMR nuclear magnetic resonance
$O_2$ oxygen
pet petroleum
s singlet
sat. saturated
tert tertiary
THF tetrahydrofuran
triplet Example 1

Preparation of 4-((8-azabicyclo[3.2.1]octan-3-yloxy)methyl)-5-cyclopropyl-3-(2-(trifluoromethoxy)phenyl)isoxazole (E)-2-(trifluoromethoxy) benzaldehyde oxime

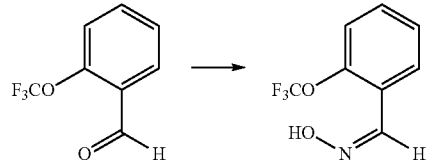 [SMILES: O=Cc1ccccc1OC(F)(F)F ; O/N=C\c1ccccc1OC(F)(F)F]

A solution of sodium hydroxide (3.75 g, 0.093 mol) in water (64 ml) was added to a stirred solution of hydroxylamine hydrochloride (6.3 g, 0.0907 mol) in water (64 ml) at 0° C. After 10 mins, a solution of 2-(trifluoromethoxy) benzaldehyde (15 g, 0.078 mol) in ethanol (64 ml) was added. The resulting solution was allowed to stir for an additional 1 h at room temperature. The resulting solution was diluted with ice water, extracted with ethyl acetate and the combined organic layer was washed with brine, dried over anhydrous sodium sulfate, filtered and the filtrate concentrated under reduced pressure to afford the titled compound (16.5 g, 86%) as a solid. $^1$H NMR (400 MHz, $d^6$-DMSO): δ 11.75 (s, 1H), 8.22 (s, 1H), 7.60-7.38 (m, 3H). 8.23 (S, 1H), 7.88 (dd, J=8.0 Hz, J=2 Hz, 1H), 7.59-7.51 (m, 1H), 7.49-7.42 (m, 2H).

(Z)-N-hydroxy-2-(trifluoromethoxy) benzimidoyl chloride

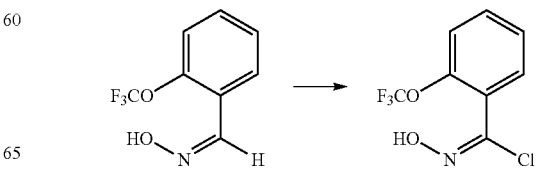

N-chlorosuccinimide (12 g, 0.0901 mol) was slowly added to a solution of (E)-2-(trifluoromethoxy) benzaldehyde oxime (16.5 g, 0.0804 mol) in N, N-dimethylformamide (165 ml) at room temperature. After 1 h the solution was diluted with water and extracted with ethyl acetate. The combined organic layers were washed with brine, dried over anhydrous $Na_2SO_4$, filtered and concentrated under reduced pressure to afford the titled compound (20 g, 92%) as a solid. $^1$H NMR (400 MHz, d$^6$-DMSO): δ 12.65 (s, 1H), 7.72-7.64 (m, 2H), 7.51-7.49 (m, 2H).

Methyl 5-cyclopropyl-3-(2-(trifluoromethoxy)phenyl)isoxazole-4-carboxylate

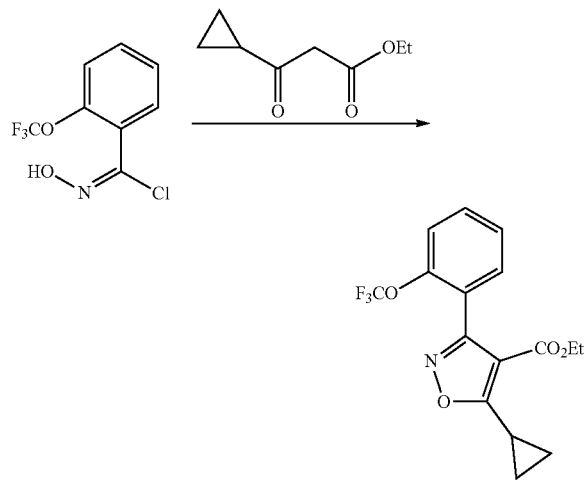

A solution of methyl 3-cyclopropyl-3-oxopropanoate (26 g, 0.166 mol) in dichloromethane (50 ml) was added to a solution of (Z)-2-(trifluoromethoxy)benzoyl chloride oxime (20 g, 0.083 mol) and triethylamine (100 ml) in dichloromethane (150 ml) at 0° C. After 10 mins the mixture was allowed to warm room temperature and stirred for a further 16 h. The reaction mixture was then diluted with water and dichloromethane, separated and the organic layer dried over anhydrous $Na_2SO_4$, filtered concentrated under reduced pressure. The crude product was purified by flash column chromatography using silica gel 100-200 mesh eluting with 20% ethyl acetate in petroleum ether to afford the titled compound (12 g, 44%) as a solid. LC-MS: 2.34 mins, [M+H]$^+$ 342

(5-cyclopropyl-3-(2-(trifluoromethoxy)phenyl)isoxazol-4-yl) methanol

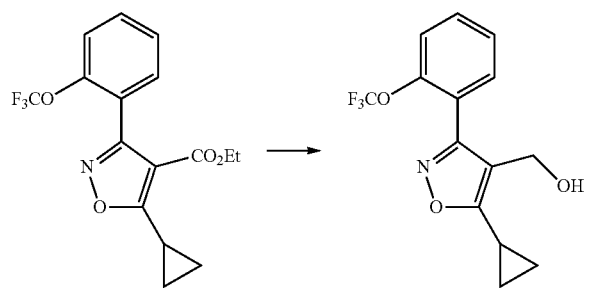 [SMILES: CCOC(=O)c1c(-c2ccccc2OC(F)(F)F)noc1C1CC1 ; OCc1c(-c2ccccc2OC(F)(F)F)noc1C1CC1]

2M Lithium aluminium hydride in THF (50 ml, 0.1009 mol) was added dropwise to a solution of methyl 5-cyclopropyl-3-(2-(trifluoromethoxy) phenyl) isoxazole-4-carboxylate (12 g, 0.035 mol) in tetrahydrofuran (120 ml), under nitrogen at −10° C. After 30 mins ethyl acetate, water and 15% aq. sodium hydroxide were added and the resulting mixture filtered and washed with ethyl acetate. The filtrate was washed with brine, dried over anhydrous $Na_2SO_4$, filtered and concentrated under reduced pressure to afford the titled compound (9.5 g, 31%) as an oil. LC-MS; 2.03 mins, [M+H]$^+$ 300

4-(bromomethyl)-5-cyclopropyl-3-(2-(trifluoromethoxy)phenyl)isoxazole

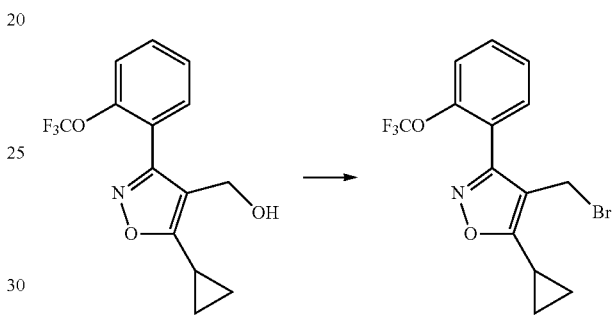

A solution of carbon tetrabromide (15.8 g, 0.0476 mol) in dichloromethane (50 ml) was added drop wise to a solution of triphenylphosphine (12.5 g, 0.047 mol) and (5-cyclopropyl-3-(2-(trifluoromethoxy) phenyl) isoxazol-4-yl) methanol (9.5 g, 0.0317 mol) in dichloromethane (100 ml) at room temperature. After 1 h the reaction mixture was concentrated under reduced pressure and purified by flash column chromatography using silica gel 100-200 mesh, eluting with 35% ethyl acetate in petroleum ether to afford the titled compound (7 g, 60%) as an oil. $^1$H NMR (400 MHz, CDCl$_3$): δ 7.64-7.53 (m, 2H), 7.46-7.38 (m, 2H), 4.33 (s, 2H), 2.16-2.06 (m, 1H), 1.32-1.23 (m, 2H), 1.22-1.15 (m, 2H).

4-((8-azabicyclo[3.2.1]octan-3-yloxy)methyl)-5-cyclopropyl-3-(2-(trifluoromethoxy)phenyl)isoxazole

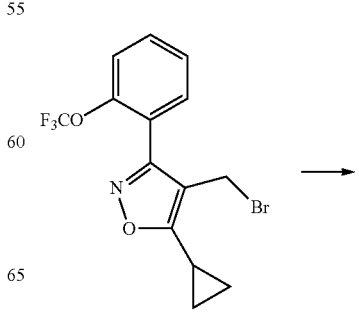

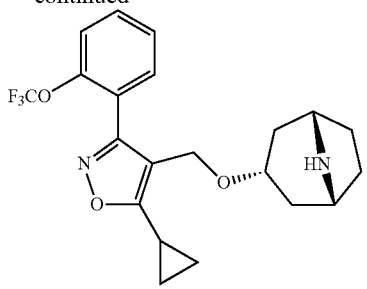

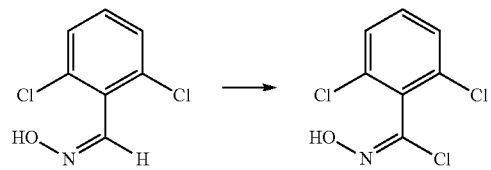

2,6-dichloro-N-hydroxybenzimidoyl chloride

18-Crown-6 (5.6 g, 0.021 mol) and potassium tert-butoxide (4.7 g, 0.042 mol) were added to a solution of N-Boc-nortropine (4.8 g, 0.021 mol) in tetrahydrofuran (100 ml). After 1 h, a solution of 4-(bromomethyl)-5-cyclopropyl-3-(2-(trifluoromethoxy)-phenyl) isoxazole (7 g, 0.019 mol) in tetrahydrofuran (40 ml) was added drop wise at room temperature. After 16 h the reaction mixture was concentrated, diluted with water and ethyl acetate, separated and the organic layer washed with brine, dried over anhydrous $Na_2SO_4$, filtered and concentrated under reduced pressure. The crude product was purified by flash column chromatography using silica gel 100-200 mesh eluting with 0-100% ethyl acetate in petroleum ether to afford tert-butyl 3-((5-cyclopropyl-3-(2-(trifluoromethoxy)phenyl)isoxazol-4-yl)methoxy)-8-azabicyclo[3.2.1]octane-8-carboxylate (7 g, 71%) as an oil. This was dissolved in dichloromethane (80 ml) and trifluoroacetic acid (20 ml) was added at room temperature. After 1 h, the reaction mixture was evaporated under reduced pressure, the residue was dissolved in ethyl acetate, washed with a saturated sodium bicarbonate solution, the organic layer was then dried over anhydrous $Na_2SO_4$, filtered and the filtrate was concentrated under reduced pressure to afford the titled compound (5.4 g, 70%) as a colourless oil. LC-MS: 1.81 mins, $[M+H]^+$ 409

Example 2

Preparation of (5-cyclopropyl-3-(2,6-dichlorophenyl)isoxazol-4-yl)methanol

2,6-dichlorobenzaldehyde oxime

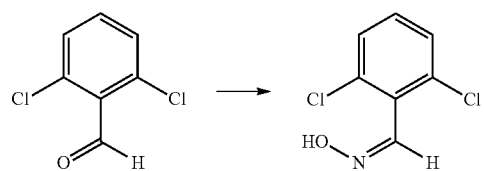 [SMILES: O=Cc1c(Cl)cccc1Cl ; O/N=C\c1c(Cl)cccc1Cl]

3N Sodium hydroxide (8.35 g, 0.208 mol) was added drop wise to a solution of hydroxylamine hydrochloride (14.51 g, 0.208 mol) in water (130 ml) at 0° C. A solution of 2,6-dichloro-benzaldehyde (32.0 g, 0.182 mol) in ethanol (250 ml) was then added and the reaction mixture heated at 90° C. for 16 h. The mixture was then cooled to room temperature, concentrated to dryness and the crude product triturated with 10:1 water/EtOH, filtered and dried under reduced pressure to afford the titled compound as a solid (27.0 g, 78% yield). $^1$H NMR (400 MHz, $d^6$-DMSO): δ 11.79 (s, 1H), 8.22 (s, 1H), 7.60-7.38 (m, 3H).

N-chlorosuccinimide (19.06 g, 0.1428 mol) was added portion wise to a solution of 2, 6-dichlorobenzaldehyde oxime (27 g, 0.1428 mole) in DMF (300 ml). After 2 h the reaction was poured into water and the product extracted with ethyl acetate. The combined organic layers were washed with water, brine and dried over anhydrous sodium sulfate. After filtering, the solvent was removed under reduced pressure to afford the titled compound as yellow oil (29 g, 90%). $^1$H NMR (400 MHz, $d^6$-DMSO): δ 12.68 (s, 1H), 7.72-7.52 (m, 3H).

Ethyl 5-cyclopropyl-3-(2,6-dichlorophenyl)isoxazole-4-carboxylate

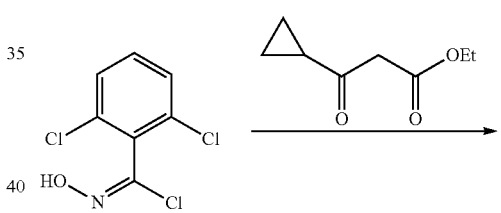

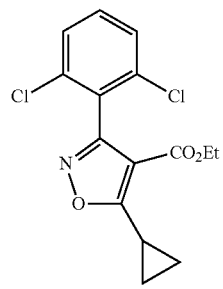

Triethylamine (110 ml) was added to a stirred solution of 2,6-dichloro-N-hydroxybenzimidoyl chloride (25 g, 0.129 mol) and ethyl 3-cyclopropyl-3-oxopropanoate 4 (100 g, 0.70 mol) in dichloromethane (100 ml) at room temperature. After 16 h the mixture was concentrated under reduced pressure and purified by chromatography on silica gel, eluting with 10% EtOAc in petroleum ether to afford the titled compound as a solid (27 g, 75%). LC-MS: 2.85 mins, $[M+H]^+$ 326

(5-cyclopropyl-3-(2,6-dichlorophenyl)isoxazol-4-yl)methanol

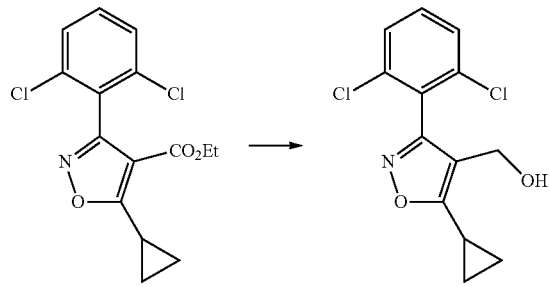 [SMILES: CCOC(=O)c1c(-c2c(Cl)cccc2Cl)noc1C1CC1 ; OCc1c(-c2c(Cl)cccc2Cl)noc1C1CC1]

1N DIBAL-H in hexane (270 ml, 0.274 mol) added dropwise to a solution of ethyl-5-cyclopropyl-3-(2,6-dichlorophenyl)isoxazole-4-carboxylate (27 g, 0.083 mol) in tetrahydrofuran (300 ml) at −70 to −75° C. The mixture then allowed to warm to room temperature and stirred for a further 16 h. The reaction mixture was then quenched with sat. ammonium chloride solution, filtered and the residue washed with ethylacetate. The filtrate was dried and concentrated under reduced pressure to afford the titled compound as a solid (21 g, 89%). LC-MS: 2.25 mins, [M+H]$^+$ 284.

Example 3

Preparation of (4-((4-bromo-3-chlorophenoxy)methyl)-5-cyclopropyl-3-(2,6-dichlorophenyl)isoxazole

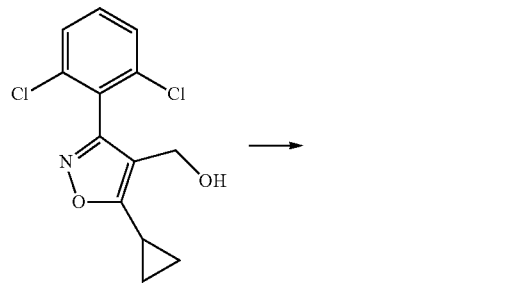

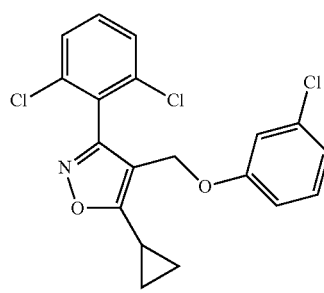

Thionylchloride (62 ml, 0.52 mol) was added slowly to a solution of (5-cyclopropyl-3-(2,6-dichlorophenyl)isoxazol-4-yl)methanol (21 g, 0.073 mol) in dichloromethane (100 ml) at 0-5° C. The reaction mixture was then allowed to warm to 25-30° C. and stirred for a further 2 h before being concentrated under reduced pressure. The crude product was then added to a mixture of bromo-3-chloro-phenol (16.2 g 0.081 mol), potassium carbonate (67 g 0.48 mol) and sodium iodide (19 g 0.12 mol) in DMF (100 ml). The mixture was heated at 60-65° C. for 16 h, poured into water (500 ml) and extracted with ethyl acetate (600 ml). The organic layers were washed with water, brine, dried, concentrated under reduced pressure and the crude product purified by chromatography on silica gel eluting with 20% EtOAc in petroleum ether to afford the titled compound as a solid (18 g, 60%). LC-MS: 2.63 mins, [M+H]$^+$ 472

Example 4

Preparation of Sodium 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-sulfinate 2,6-dibromo-4-fluorobenzo[d]thiazole

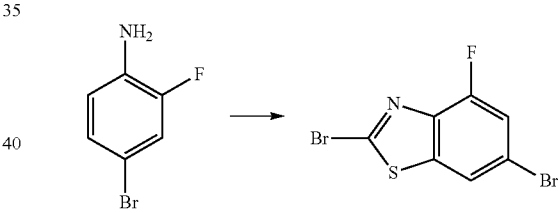

A solution of bromine (7 ml, 0.131 mol) in acetic acid (50 ml) was added to a solution of 4-bromo-2-fluoro aniline (25 g, 0.131 mol) and sodium thiocyanide (43 g, 0.526 mol) in acetic acid (200 ml) at 0° C. and the resulting mixture then warmed to 40° C. After 16 h the reaction mixture was diluted with ice water and the pH adjusted to 8-9 with ammonium hydroxide solution. The resulting mixture was filtered and the remaining solid dried to afford crude 6-bromo-4-fluorobenzo[d]thiazol-2-amine as a solid. The product was dissolved in acetonitrile (60 ml) at 0° C. before tert-butyl nitrite (3.6 ml) and then copper (II) bromide (5.41 g, 0.024 mol) were added. The reaction mixture was warmed to 40° C. and after 16 h the reaction mixture was diluted with ethyl acetate, washed with water and the organic layer dried over anhydrous Na$_2$SO$_4$, filtered and concentrated under reduced pressure to afford the titled compound (4 g, 10%) as a solid. LC-MS: 2.37 mins, [M+H]$^+$ 310

33

4-((8-(6-bromo-4-fluorobenzo[d]thiazol-2-yl)-8-azabicyclo[3.2.1]octan-3-yloxy)methyl)-5-cyclopropyl-3-(2-(trifluoromethoxy)phenyl)isoxazole

34

Methyl 3-(2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazol-6-ylsulfonyl)propanoate

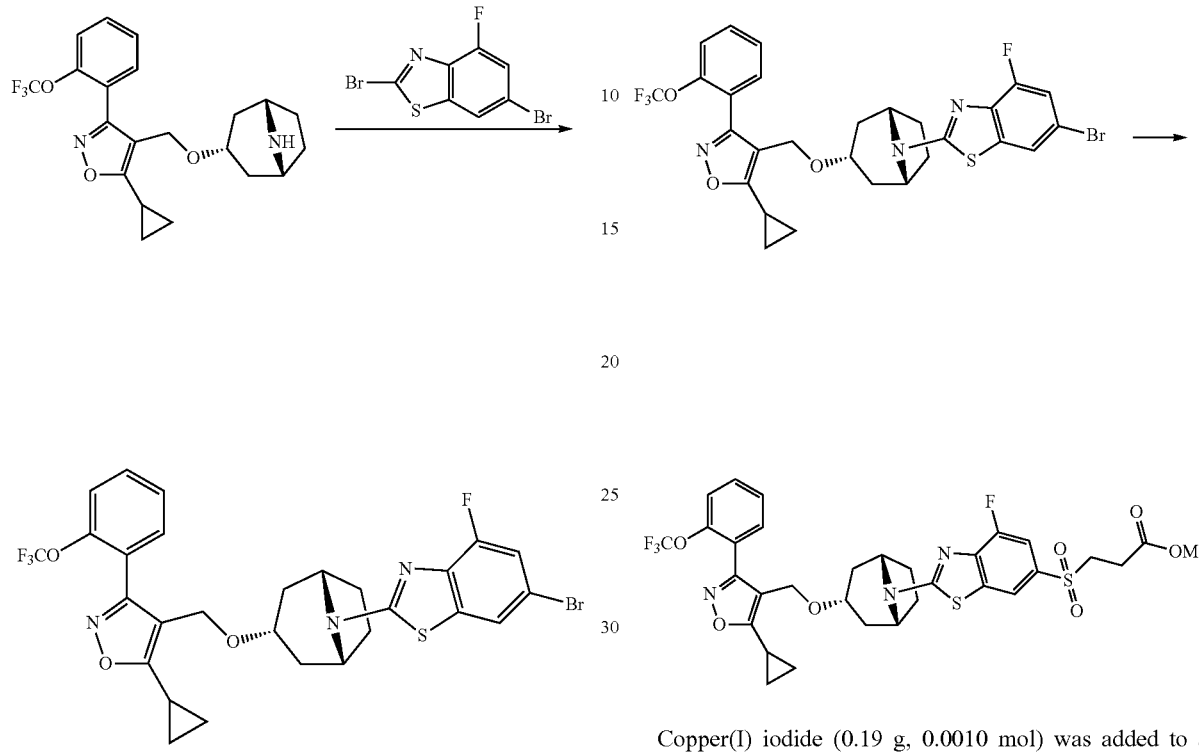

Potassium carbonate (0.86 g, 0.0062 mol) was added to a solution of 4-((8-azabicyclo[3.2.1]octan-3-yloxy)methyl)-5-cyclopropyl-3-(2-(trifluoromethoxy)phenyl) isoxazole (0.85 g, 0.0020 mol) and 2,6-dibromo-4-fluorobenzo[d]thiazole (0.64 g, 0.0020 mol) in DMF (16 ml) at room temperature. After 16 h, the reaction mixture was poured into ice water and extracted with ethyl acetate. The combined organic layers were washed with brine, dried over anhydrous $Na_2SO_4$, filtered, concentrated under reduced pressure and purified by column chromatography using silica gel 100-200 mesh eluting with 80% ethyl acetate in petroleum ether to afford 4 the titled compound (0.75 g, 57%) as a solid. $^1$H NMR (400 MHz, $d^6$-DMSO): δ 7.88-7.85 (m, 1H), 7.72-7.62 (m, 2H), 7.58-7.54 (m, 2H), 7.41 (dd, J=10.4 Hz, J=2 Hz, 1H), 4.34 (s, 2H), 4.22-4.15 (m, 2H), 3.59-3.51 (m, 1H), 2.40-2.28 (m, 1H), 2.02-1.92 (m, 2H), 1.86-1.78 (m, 4H), 1.77-1.68 (m, 2H), 1.18-1.04 (m, 4H).

Copper(I) iodide (0.19 g, 0.0010 mol) was added to a solution of 4-((8-(6-bromo-4-fluorobenzo[d]thiazol-2-yl)-8-azabicyclo[3.2.1]octan-3-yloxy)methyl)-5-cyclopropyl-3-(2-(trifluoromethoxy)phenyl)isoxazole (0.65 g, 0.0010 mol), sodium 3-methoxy-3-oxopropane-1-sulfinate (0.35 g, 0.0020 mol) and L-proline (0.117 g, 0.0010 mol) in dimethylsulfoxide (13 ml) at room temperature and the resulting mixture warmed to 130° C. After 16 h, water and ethyl acetate were added and the mixture filtered through celite. The filtrate was then washed with cold water, brine, dried over anhydrous $Na_2SO_4$, filtered, concentrated under reduced pressure and purified by flash column chromatography using silica gel 100-200 mesh, eluting with 0-70% ethyl acetate in petroleum ether to afford the titled compound (0.15 g, 20%) as a solid. LC-MS: 2.50 mins, [M+H]$^+$ 710

Sodium 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-sulfinate

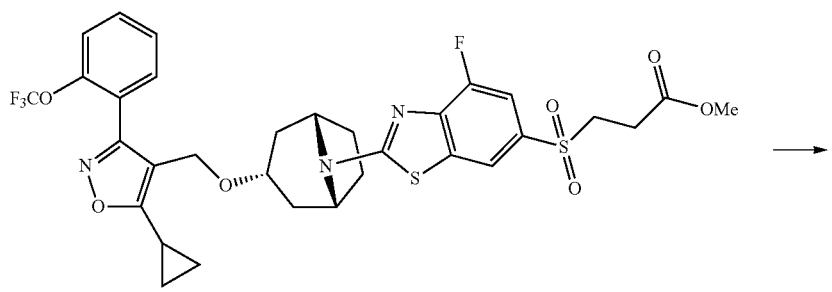

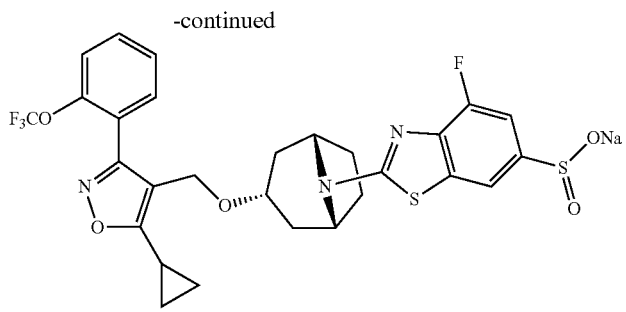

1M Sodium methoxide in methanol (0.5 ml) was added to a solution of methyl 3-(2-(3-(((5-cyclopropyl-3-(2-(trifluoromethoxy)phenyl)isoxazol-4-yl)methoxy)-8-azabicyclo[3.2.1]octan-8-yl)-4-fluorobenzo[d]thiazol-6-ylsulfonyl)propanoate (0.15 g, 0.0002 mol) in methanol (2 ml) at 0° C. After 5 h at room temperature, the reaction mixture was concentrated, triturated with diethyl ether, washed with n-pentane and dried under reduced pressure to afford the titled compound (0.102 g, 75%) as a solid. LC-MS: 4.85 mins, [M-Na+H]$^+$ 624; $^1$H NMR (400 MHz, d$^6$-DMSO): δ 7.72-7.62 (m, 2H), 7.59-7.52 (m 3H), 7.09 (d, J=10.4 Hz, 1H), 4.33 (s, 2H), 4.18-4.12 (m, 2H), 3.58-3.54 (m, 1H), 2.40-2.30 (m, 1H), 2.06-1.96 (m, 2H), 1.88-1.76 (m, 4H), 1.74-1.66 (m, 2H), 1.18-1.06 (m, 4H).

Example 5

2,6-Dibromo-4-methylbenzo[d]thiazole

A solution of bromine (2.7 ml, 53.76 mmol) in acetic acid (20 ml) was added to a solution of 4-bromo-2-fluoro aniline (10 g, 53.76 mmol) and sodium thiocyanide (17.4 g, 215 mmol) in acetic acid (80 ml) at 0° C. and the resulting mixture then warmed to 40° C. After 16 h the reaction mixture was diluted with ice water and the pH adjusted to 8-9 with ammonium hydroxide solution. The resulting mixture was filtered and the remaining solid dried to afford crude 6-bromo-4-methylbenzo[d]thiazol-2-amine (3.2 g) as a solid. The 6-bromo-4-methylbenzo[d]thiazol-2-amine (3 g) was dissolved in acetonitrile (60 ml) at 0° C. before tert-butyl nitrite (3.84 ml) and then a solution of copper (II) bromide (5.88 g, 223 mmol) in acetonitrile (60 ml) were added. The reaction mixture was warmed to 40° C. and after 16 h the reaction mixture was diluted with ethyl acetate, washed with water and the organic layer dried over anhydrous Na$_2$SO$_4$, filtered and concentrated under reduced pressure to afford the titled compound (1.4 g, 35%) as a solid. LC-MS: 2.49 mins, [M+H]$^+$ 308

4-((8-(6-bromo-4-methylbenzo[d]thiazol-2-yl)-8-azabicyclo[3.2.1]octan-3-yloxy)methyl)-5-cyclopropyl-3-(2-(trifluoromethoxy)phenyl)isoxazole

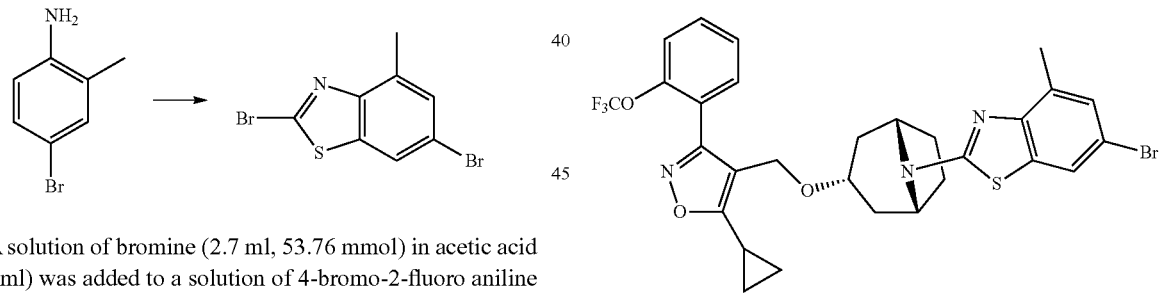

Potassium carbonate (1.5 g, 11.02 mmol) was added to a stirred solution of 4-((8-azabicyclo[3.2.1]octan-3-yloxy)methyl)-5-cyclopropyl-3-(2-(trifluoromethoxy)phenyl)isoxazole (1.5 g, 3.67 mmol) and 2,6-Dibromo-4-methylbenzo[d]thiazole (1.12 g, 3.67 mmol) in N,N-dimethylformamide (20 ml) at room temperature. After 16 h the reaction mixture was poured into ice water, extracted with ethyl acetate, the combined organic layers washed with brine, dried over anhydrous Na$_2$SO$_4$, filtered, concentrated under reduced pressure and purified by flash column chromatography using silica gel 100-200 mesh, eluting with 73% ethyl acetate in petroleum ether to afford the titled compound (1.06 g, 46%) as a solid. LC-MS: 3.06 mins, [M+H]$^+$ 636

Methyl 3-(2-(3-((5-cyclopropyl-3-(2-(trifluoromethoxy)phenyl)isoxazol-4-yl) methoxy)-8-azabicyclo[3.2.1]octan-8-yl)-4-methylbenzo[d]thiazol-6-ylsulfonyl)propanoate

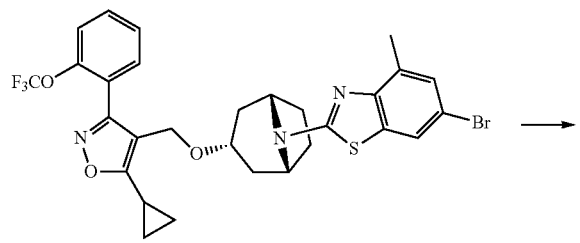

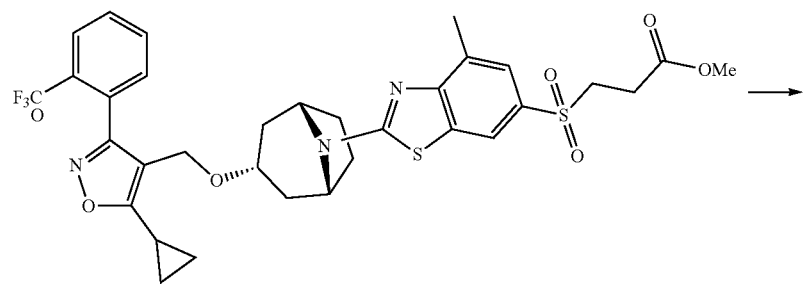

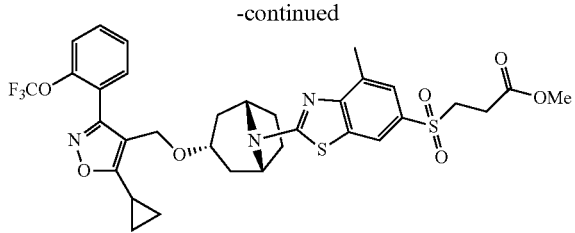

Cu(I)I (570 mg, 3.02 mmol) was added to a solution of 4-((8-(6-bromo-4-methylbenzo[d]thiazol-2-yl)-8-azabicyclo[3.2.1]octan-3-yloxy)methyl)-5-cyclopropyl-3-(2-(trifluoromethoxy)phenyl)isoxazole_(960 mg, 1.51 mmol), sodium 3-methoxy-3-oxopropane-1-sulfinate (790 mg, 4.54 mmol) and L-proline (174 mg, 1.51 mmol) in dimethylsulfoxide (20 ml) at room temperature and the resulting mixture warmed to 130° C. After 16 h, water and ethyl acetate were added and the mixture filtered through celite. The filtrate was then washed with cold water, brine, dried over anhydrous Na$_2$SO$_4$, filtered, concentrated under reduced pressure and purified by flash column chromatography using silica gel 100-200 mesh, eluting with 0-65% ethyl acetate in petroleum ether to afford the titled compound (0.25 g, 25%) as a solid. LC-MS: 2.57 mins, [M+H]$^+$ 706

Sodium 2-(3-((5-cyclopropyl-3-(2-(trifluoromethoxy)phenyl)isoxazol-4-yl)methoxy)-8-azabicyclo[3.2.1]octan-8-yl)-4-methylbenzo[d]thiazole-6-sulfinate

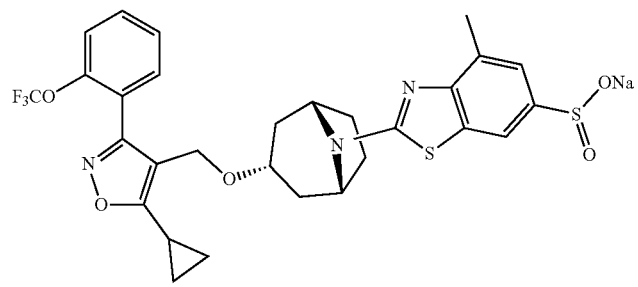

1M Sodium methoxide in methanol (7 ml) was added to a solution of methyl 3-(2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazol-6-ylsulfonyl)propanoate (0.25 g, 0.35 mmol) in methanol (2.5 ml) at 0° C. After 5 h at room temperature, the reaction mixture was concentrated, triturated with diethyl ether, washed with n-pentane and dried under reduced pressure to afford the titled compound (0.112 g, 51%) as a solid. LC-MS: 4.91 mins, [M-Na]$^+$ 618; $^1$H NMR (400 MHz, d$^6$-DMSO): 7.72-7.62 (m, 2H), 7.59-7.52 (m, 3H), 7.16-7.12 (m, 1H), 4.33 (s, 2H), 4.20-4.10 (m, 2H), 3.58-3.51 (m, 1H), 2.42 (s, 3H), 2.39-2.30 (m, 1H), 2.08-1.98 (m, 2H), 1.85-1.77 (m, 4H), 1.75-1.65 (m, 2H), 1.18-1.05 (m, 4H).

Example 6

Preparation of Sodium 3-(3-(2-chloro-4-((5-cyclopropyl-3-(2,6-dichlorophenyl)isoxazol-4-yl)methoxy)phenyl)-3-hydroxyazetidin-1-yl)benzenesulfinate 1-(3-bromophenyl)azetidin-3-ol

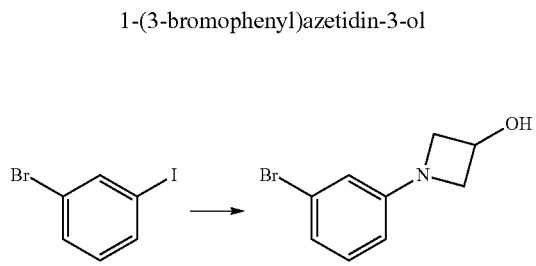

Copper (I) iodide (1.32 g, 7.34 mmol) was added to a solution of 1-bromo-3-iodobenzene (16 g, 56.53 mmol), azetidin-3-ol hydrochloride (6 g, 56.53 mmol), cesium carbonate (31 g, 96.11 mmol) and L-proline (0.66 g, 15.26 mmol) in dimethylsulfoxide (150 ml) at room temperature. The resulting mixture was then heated at 130° C. for 16 h, partitioned with water and ethyl acetate, filtered and the combined the organic layers washed with water, brine and purified by silica gel column chromatography eluting with 0-60% ethyl acetate in petroleum ether to afford the titled compound (8 g, 62.5%) as a solid. LC-MS: 3.44 mins, [M+H]+ 228

1-(3-bromophenyl)azetidin-3-one

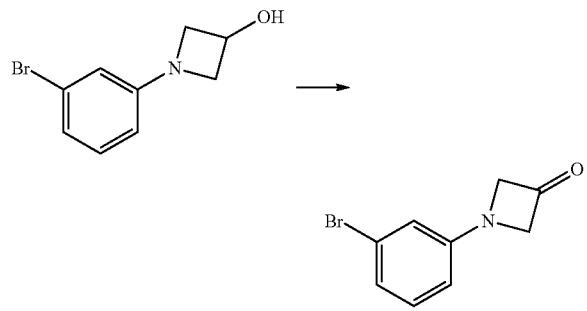

DMSO (7.4 ml, 105 mmol) was slowly added to a solution of oxalyl chloride (6.1 ml, 70.48 mmol) in dichloromethane (160 ml) at −78° C., followed by the dropwise addition of 1-(3-bromophenyl)azetidin-3-ol (8.0 g, 35.24 mmol) in dichloromethane (15 ml). After 45 min, Et$_3$N (30 ml, 211 mmol) was added and the resulting mixture stirred for a further 1 h at −78° C. The mixture was then allowed to warm gradually to 0° C., kept at this temperature for an additional 30 min, quenched by addition of sat. aq. NaHCO$_3$ and extracted with dichloromethane. The combined organic layers were dried over anhydrous Na$_2$SO$_4$, filtered and evaporated under reduced pressure to afford the titled compound as a yellow oil (5 g, 63%). LC-MS: 3.79 mins, [M+H]+ 226

1-(3-bromophenyl)-3-(2-chloro-4-((5-cyclopropyl-3-(2,6-dichlorophenyl)isoxazol-4-yl)methoxy)phenyl)azetidin-3-ol

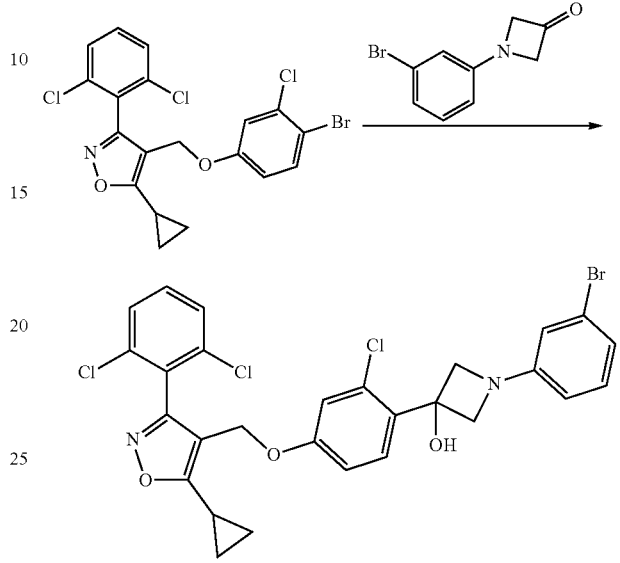

2.5M n-BuLi, in hexane (5.8 ml, 14.587 mmol) was added to a solution of 4-((4-bromo-3-chlorophenoxy)methyl)-5-cyclopropyl-3-(2,6-dichlorophenyl)isoxazole (4.6 g, 9.725 mmol) in THF (92 ml) at −78° C. After 30 mins, 1-(3-bromophenyl)azetidin-3-one (1.7 g, 7.780 mmol) was added and the resulting mixture stirred at −78° C. for a further 1 h. The reaction mixture was then partitioned with sat. aq. ammonium chloride and ethyl acetate. The organic layer was washed with water and brine solution, dried over anhydrous Na$_2$SO$_4$, filtered, concentrated under reduced pressure and the crude product purified by silica gel column chromatography eluting with 0-50% ethyl acetate in petroleum ether to afford the titled compound (1.6 g, 30%) as a white solid. LC-MS: 2.58 mins, [M+H]+ 619

Methyl 3-(3-(3-(2-chloro-4-((5-cyclopropyl-3-(2,6-dichlorophenyl)isoxazol-4-yl)methoxy) phenyl)-3-hydroxyazetidin-1-yl)phenylsulfonyl)propanoate

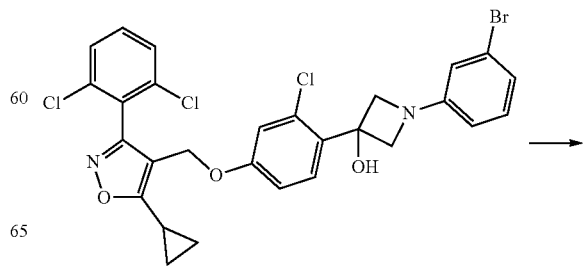

-continued

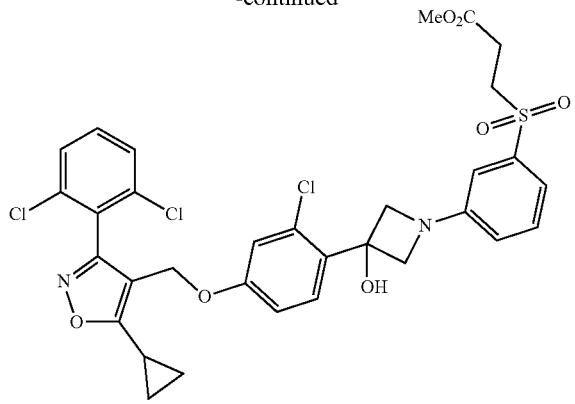

Copper(I) iodide (0.96 g, 5.16 mmol) was added to a solution of 1-(3-bromophenyl)-3-(2-chloro-4-((5-cyclopropyl-3-(2,6-dichlorophenyl)isoxazol-4-yl)methoxy)phenyl) azetidin-3-ol (1.6 g, 2.58 mmol), sodium 3-methoxy-3-oxopropane-1-sulfinate (1.34 g, 7.74 mol) and L-proline (0.28 g, 2.4 mmol) in dimethylsulfoxide (32 ml) to room temperature. The resulting mixture was stirred at 130° C. for 16 h then partitioned with water and ethyl acetate before being filtered through celite. The combined organic layers were washed with cold water and brine solution, dried over anhydrous Na$_2$SO$_4$, filtered, concentrated under reduced pressure and purified by silica gel column chromatography eluting with 0-60% ethyl acetate in petroleum ether to afford the titled compound (320 mg, 18%) as a solid. LC-MS: 2.35 mins, [M+H]$^+$ 691

Sodium 3-(3-(2-chloro-4-((5-cyclopropyl-3-(2,6-dichlorophenyl)isoxazol-4-yl)methoxy)phenyl)-3-hydroxyazetidin-1-yl)benzenesulfinate

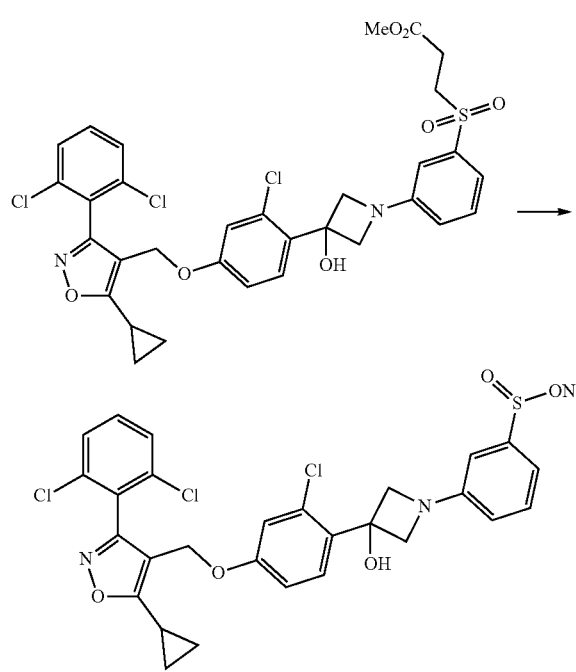

1M NaOMe in methanol (5 ml, 4.6 mmol) was added to a mixture of methyl 3-(3-(3-(2-chloro-4-((5-cyclopropyl-3-(2,6-dichlorophenyl)isoxazol-4-yl)methoxy)phenyl)-3-hydroxyazetidin-1-yl)phenylsulfonyl) propanoate (0.32 g, 0.46 mmol) in methanol (5 ml) at 0° C. After 5 h at room temperature the reaction mixture was concentrated under reduced pressure, the residue triturated with diethyl ether and washed with n-pentane to afford the titled compound as a solid (0.13 g, 46%). LC-MS: 4.61 mins, [M–H]$^+$ 603; $^1$H NMR (400 MHz, d$^6$-DMSO): δ 7.64-7.58 (m, 2H), 7.52 (dd, J=9.2 Hz, J=7.2 Hz, 1H), 7.36 (d, J=8.4 Hz, 1H), 7.09-7.03 (m, 1H), 6.88-6.83 (m, 1H), 6.76-6.68 (m, 2H), 6.61-6.58 (m, 1H), 6.31-6.26 (m, 1H), 4.89 (s, 2H), 4.21 (d, 2H), 3.98-3.92 (m, 2H), 2.48-2.40 (m, 1H), 1.20-1.09 (m, 4H).

Example 7

Preparation of Sodium 4-(3-(2-chloro-4-((5-cyclopropyl-3-(2,6-dichlorophenyl)isoxazol-4-yl) methoxy)phenyl)-3-hydroxycyclobutyl)benzenesulfinate 3-(4-bromophenyl)cyclobutanone

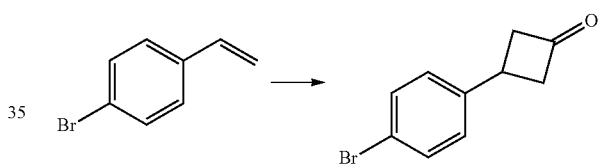

Active zinc powder (10.7 g, 163 mmol) and then trichloroacetyl chloride (24.8 g, 136 mmol) were added to a solution of 1-bromo-4-vinylbenzene (10 g, 54.64 mmol) in dry diethyl ether (300 ml) at 0° C. The reaction mixture was warmed to reflux for 4 h, cooled to room temperature, filtered and the organic phase quenched with sat. NaHCO$_3$. The resulting mixture was extracted ethyl acetate, the combined organic phases dried over MgSO$_4$, filtered and concentrated under reduced pressure to give crude 3-(4-bromophenyl)-2,2-dichlorocyclobutanone. This was dissolved in acetic acid (136 ml) and cooled to 0° C. before active zinc powder (10.2 g, 157 mmol) was added. The reaction mixture was then warmed at reflux for 16 h, filtered, the filtrate neutralized with aq. 2M NaOH and extracted diethyl ether. The organic layer was washed with brine, dried over MgSO$_4$, concentrated under reduced pressure and purified by silica gel column chromatography eluting with 0-50% ethyl acetate in petroleum ether to afford the titled compound (8 g, 66%) as a solid. $^1$H NMR (400 MHz, d$^6$-DMSO): δ 7.56-7.51 (m, 2H), 7.38-7.32 (m, 2H), 3.70-3.59 (m, 1H), 3.48-3.39 (m, 2H), 3.25-3.16 (m, 2H).

3-(4-bromophenyl)-1-(2-chloro-4-((5-cyclopropyl-3-(2,6-dichlorophenyl)isoxazol-4-yl)methoxy)phenyl)cyclobutanol

Methyl 3-(4-(3-(2-chloro-4-((5-cyclopropyl-3-(2,6-dichlorophenyl)isoxazol-4-yl)methoxy) phenyl)-3-hydroxycyclobutyl)phenylsulfonyl)propanoate

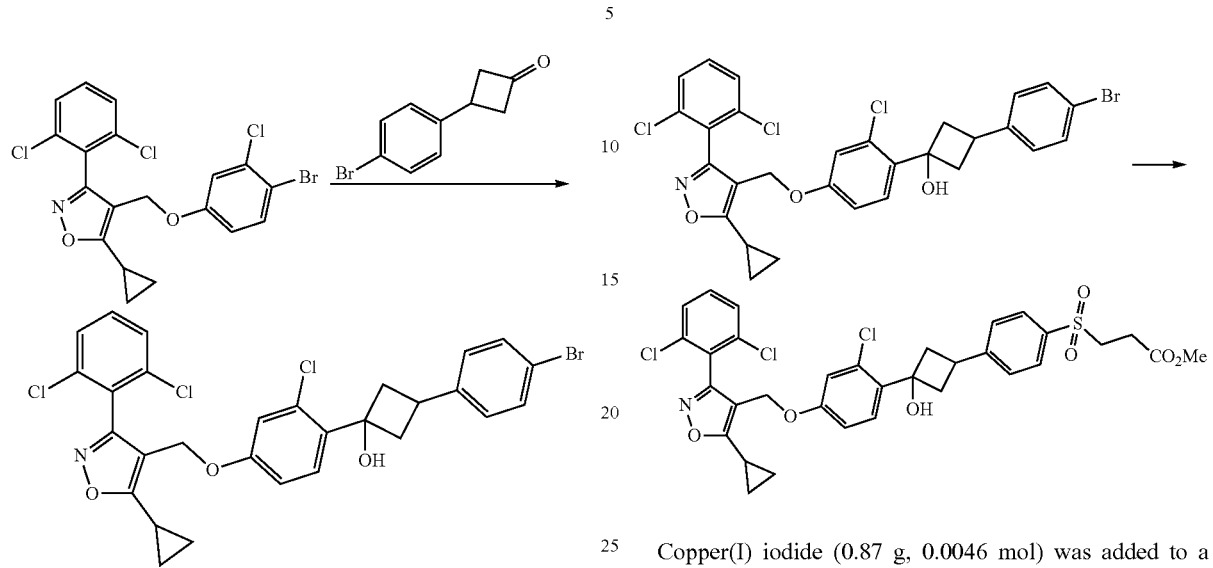

2.5M n-BuLi in hexane (6.3 ml, 15.8 mmol) was added to a solution of 4-(4-bromo-3-chlorophenoxy)methyl)-5-cyclopropyl-3-(2,6-dichlorophenyl)isoxazole (5 g, 10.57 mmol) in THF (100 ml) at −78° C. After 30 min 3-(4-bromophenyl)cyclobutanone (1.9 g, 8.456 mmol) was added and the reaction mixture kept at −78° C. for 1 h before being partitioned with saturated ammonium chloride and ethyl acetate. The organic layer was washed with cold water, brine, dried over anhydrous Na$_2$SO$_4$, filtered, concentrated under reduced pressure and purified using silica gel column chromatography, eluting with 0-50% ethyl acetate in petroleum ether to afford the title compound (1.2 g, 18%) as a solid. $^1$H NMR (400 MHz, d$^6$-DMSO): δ 7.47-7.38 (m, 5H), 7.33 (dd, J=8.8. Hz, J=6.8 Hz, 1H), 7.17-7.13 (m, 2H), 6.89 (d, J=2.8 Hz, 1H), 6.73 (dd, J=8.8 Hz, J=2.8 Hz, 1H).

Copper(I) iodide (0.87 g, 0.0046 mol) was added to a solution of 3-(4-bromophenyl)-1-(2-chloro-4-((5-cyclopropyl-3-(2,6-dichlorophenyl)isoxazol-4-yl)methoxy)phenyl)cyclobutanol (1.2 g, 0.0022 mol), sodium 3-methoxy-3-oxopropane-1-sulfinate (0.8 g, 0.0046 mol) and L-proline (1.05 g, 0.0092 mol) in dimethylsulfoxide (12 ml) at room temperature. The resulting mixture was stirred at 130° C. for 16 h before being partitioned with water and ethyl acetate. After filtering through celite the organic layer was washed with cold water, brine, and purified by silica gel column chromatography eluting with 0-70% ethyl acetate in petroleum ether to afford the titled compound (210 mg, 16%) as a solid. LC-MS: 2.40 mins, [M+H]$^+$ 690

Sodium 4-(3-(2-chloro-4-((5-cyclopropyl-3-(2,6-dichlorophenyl)isoxazol-4-yl)methoxy)phenyl)-3-hydroxycyclobutyl)benzenesulfinic acid

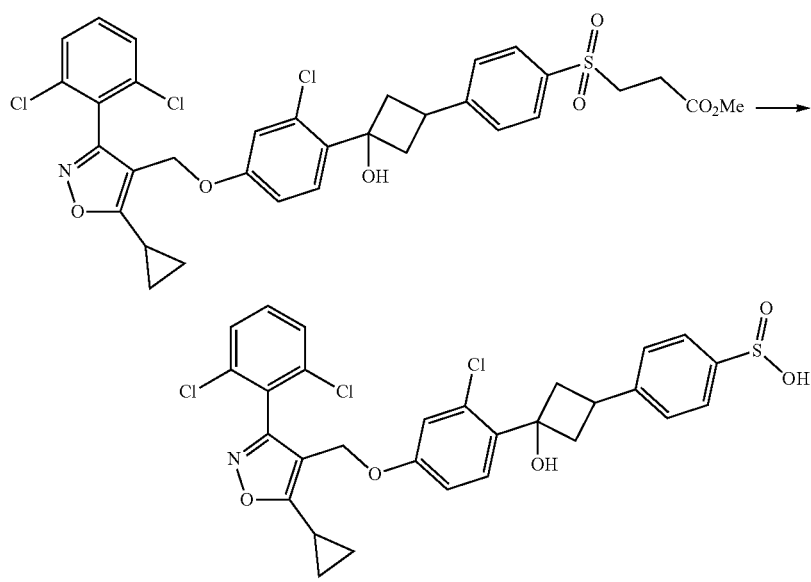

1M NaOMe in MeOH (5 ml, 28.9 mmol) was added to a stirred mixture of methyl 3-(4-(3-(2-chloro-4-((5-cyclopropyl-3-(2,6-dichlorophenyl)isoxazol-4-yl)methoxy)phenyl)-3-hydroxycyclobutyl)phenylsulfonyl) propanoate (0.21 g, 0.289 mol) in methanol (3 ml) at 0° C. The reaction mixture was stirred at room temperature for 5 h, then concentrated under reduced pressure, the residue triturated with diethyl ether and washed with n-pentane to afford 4-(3-(2-chloro-4-((5-cyclopropyl-3-(2,6-dichlorophenyl)isoxazol-4-yl)methoxy)phenyl)-3-hydroxycyclobutyl)benzenesulfinic acid as solid (0.12 g, 66%), LC-MS: 4.70 mins, [M−H]$^+$ 602; $^1$H NMR (400 MHz, d$^6$-DMSO): δ 7.66-7.61 (m, 2H), 7.58-7.51 (m, 2H), 7.34 (d, J=8 Hz, 2H), 7.19 (d, J=8 Hz, 2H), 6.91 (d, J=2.4 Hz, 1H), 6.76 (dd, J=8.4 Hz, J=2.4 Hz, 1H), 4.92 (s, 2H), 3.15-3.05 (m, 2H), 2.80-2.72 (m, 1H), 2.48-2.34 (m, 3H), 1.26-1.18 (m, 2H), 1.16-1.10 (m, 2H).

Example 8

Preparation of Sodium 4-(2-(2-chloro-4-((5-cyclopropyl-3-(2,6-dichlorophenyl)isoxazol-4-yl)methoxy)phenyl) cyclopropyl)benzenesulfinate 1-(2-(4-Bromophenyl)cyclopropyl)-2-chloro-4-methoxybenzene

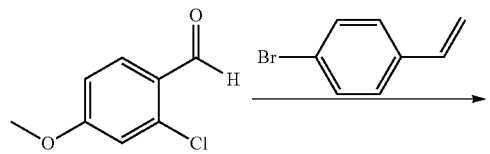

2-Chloro-4-methoxy benzaldehyde (10 g, 58.82 mmol) was added to a stirred solution of tosylhydrazide (11.6 g, 64.70 mmol) in dioxane (25 ml) at room temperature. After 3 h the reaction mixture was cooled to 0° C., filtered and the isolated solid carefully washed with cold dioxane and then hot pet ether. The intermediate was then dissolved in dioxane (100 ml) and stirred under nitrogen with potassium carbonate (12.19 g, 88.23 mmol) and 4-bromostyrene (21 g, 117.64 mmol) at 70° C. After 24 h, the reaction mixture was concentrated and purified by flash chromatography to afford the titled compound 2.2 g (19.8%) as a solid. $^1$H NMR (400 MHz, d$^6$-DMSO): δ 7.48-7.43 (m, 2H), 7.20-7.16 (m, 2H), 7.13 (d, J=8.4 Hz, 1H), 7.02 (d, J=2.8, 1H), 6.87 (dd, J=8.8 and 2.8 Hz, 1H), 3.75 (s, 3H), 2.29.-2.22 (m, 1H), 2.08-2.01 (m, 1H), 1.54-1.47 (m, 1H), 1.44-1.38 (m, 1H)

4-(2-(4-Bromophenyl)cyclopropyl)-3-chlorophenol

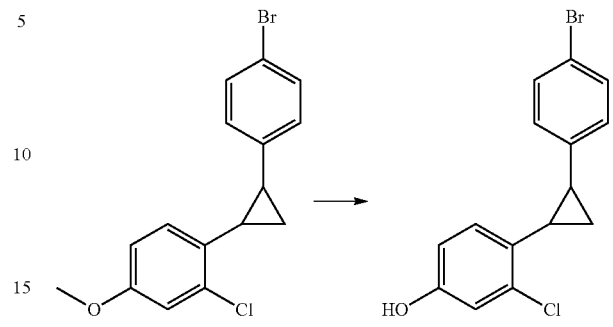

Boron tribromide (1.56 g, 6.23 mmol) was added slowly to a stirred solution of 1-(2-(4-Bromophenyl)cyclopropyl)-2-chloro-4-methoxybenzene (2.1 g, 6.23 mmol) in dichloromethane (20 ml) at 0° C. and the resulting mixture allowed to warm to room temperature. After 3 h the reaction was quenched with methanol, concentrated and the crude dissolved ethyl acetate. This was then washed with saturated sodium bicarbonate solution, saturated brine solution, dried over anhydrous Na$_2$SO$_4$, filtered and concentrated under reduced pressure. The solid was stirred in n-pentane (20 ml) for 1 h, filtered and dried under vacuum to give the titled compound (1.9 g, 95%) as a solid. LC-MS: 2.38 mins, [M−H]$^+$ 323

4-((4-(2-(4-bromophenyl)cyclopropyl)-3-chlorophenoxy)methyl)-5-cyclopropyl-3-(2,6-dichlorophenyl)isoxazole

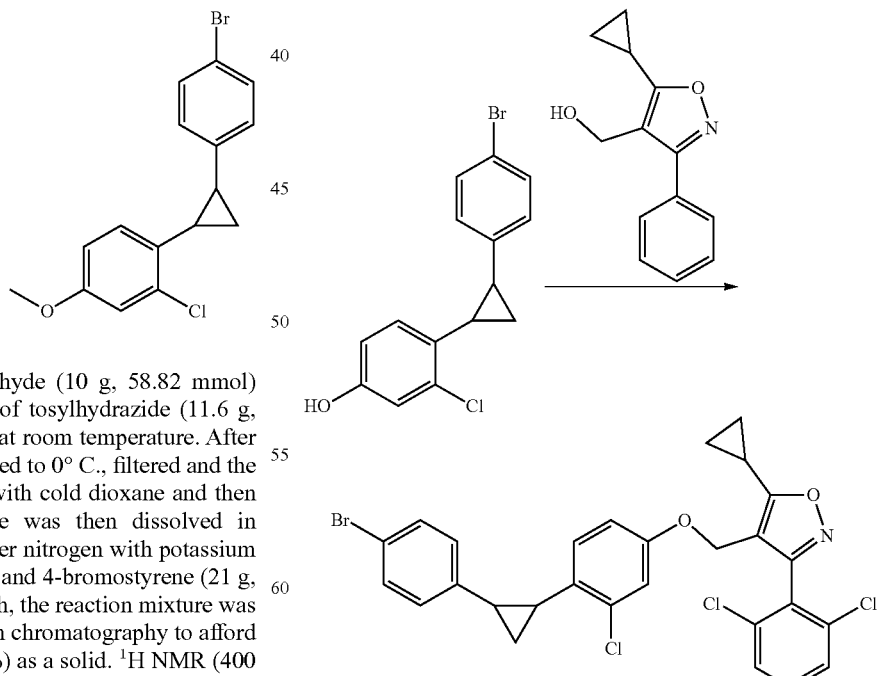

Thionylchloride (62 ml, 0.52 mol) was added slowly to a solution of (5-cyclopropyl-3-(2,6-dichlorophenyl)isoxazol- 4-yl)methanol (1.5 g, 5.3 mmol) in dichloromethane (100 ml) at 0-5° C. and the resulting mixture allowed to warm to room temperature. After 2 h the reaction mixture was concentrated under reduced pressure and dissolved in DMF (15 ml). 4-(2-(4-Bromophenyl)cyclopropyl)-3-chlorophenol (1.8 g, 5.80 mmol), potassium carbonate (4.7 g, 34.33 mmol) and sodium iodide (800 mg, 5.33 mmol) were then added and the reaction mixture heated at 60-65° C. After 16 h the reaction was poured into water, extracted with ethyl acetate, the organic layer washed with water, brine, dried over anhydrous $Na_2SO_4$, filtered, concentrated under reduced pressure and purified using silica gel column chromatography, eluting with 20% EtOAc in petroleum ether to give the titled compound (710 mg, 23%) as a solid. LC-MS: 2.76 mins, $[M+H]^+$ 588

Methyl 3-(4-(2-(2-chloro-4-((5-cyclopropyl-3-(2,6-dichlorophenyl)isoxazol-4-yl)methoxy) phenyl)cyclopropyl)phenylsulfonyl)propanoate

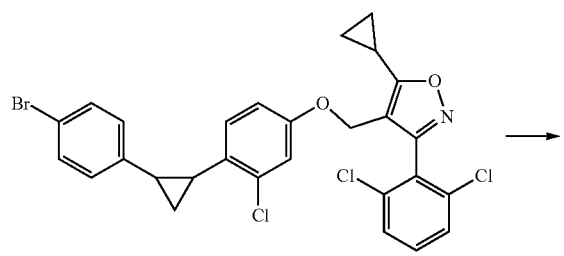

→

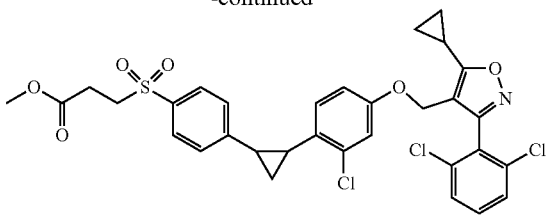

Copper(I) iodide (458 mg, 2.41 mmol) was added to a solution of 4-((4-(2-(4-bromophenyl)cyclopropyl)-3-chlorophenoxy)methyl)-5-cyclopropyl-3-(2,6-dichlorophenyl)isoxazole (710 mg, 1.20 mmol), sodium 3-methoxy-3-oxopropane-1-sulfinate (629 mg, 3.6 mmol) and L-proline (138 mg, 1.20 mmol) in dimethylsulfoxide (10 ml) at room temperature and the resulting mixture heated at 130° C. After 16 h the reaction was portioned with water and ethyl acetate before filtering through celite. The organic layer washed with cold water, brine, dried over anhydrous $Na_2SO_4$, filtered, concentrated under reduced pressure and purified using silica gel column chromatography, eluting with 0-50% pet ether and ethyl acetate to afford the titled compound (210 mg, 26%) as a solid. LC-MS: 2.50 mins, $[M+H]^+$ 680

Sodium 4-(2-(2-chloro-4-((5-cyclopropyl-3-(2,6-dichlorophenyl)isoxazol-4-yl)methoxy)phenyl)cyclopropyl)benzenesulfinate

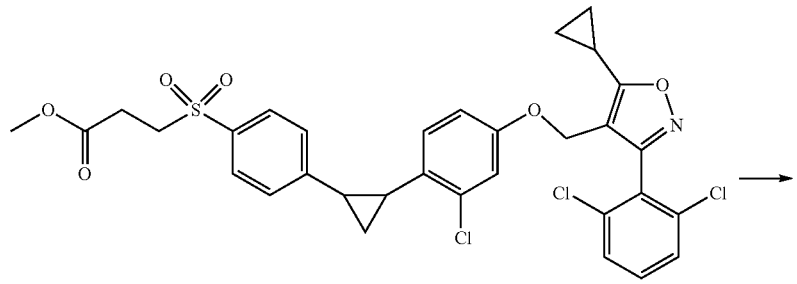

→

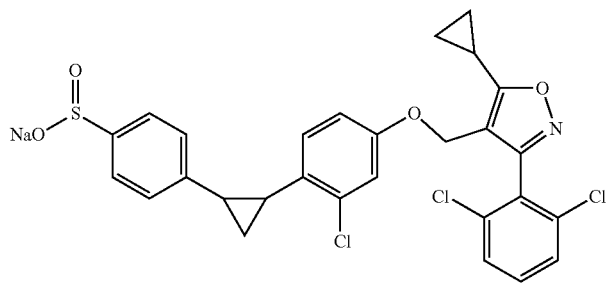

1M NaOMe in MeOH (6.3 ml, 3.1 mmol) was added to a stirred mixture of methyl 3-(4-(3-(2-chloro-4-((5-cyclopropyl-3-(2,6-dichlorophenyl)isoxazol-4-yl)methoxy)phenyl)-3-hydroxycyclobutyl)phenylsulfonyl) propanoate (0.21 g, 0.31 mol) in methanol (5 ml) at 0° C. The reaction mixture was stirred at room temperature for 5 h, then concentrated under reduced pressure, the residue triturated with diethyl ether and washed with n-pentane to afford sodium 4-(2-(2-chloro-4-((5-cyclopropyl-3-(2,6-dichlorophenyl)isoxazol-4-yl)methoxy)phenyl) cyclopropyl)benzenesulfinate as a solid (0.118 g, 65%). LC-MS: 5.01 mins, [M−H]$^+$ 574; $^1$H NMR (400 MHz, d$^6$-DMSO): δ 7.64.5.69 (m, 2H), 7.58-7.51 (m, 1H), 7.33 (d, J=8 Hz, 2H), 7.09 (d, J=8 Hz, 2H), 7.03 (d, J=8.8 Hz, 2H), 6.89 (d, J=2.4 Hz, 1H), 6.71 (dd, J=8.8 and 2.4 Hz, 1H), 5.79 (s, 2H), 2.50-2.40 (m, 1H), 2.25-2.15 (m, 1H), 2.02-1.93 (m, 1H), 1.48-1.35 (m, 2H), 1.22-1.07 (m, 4H).

Example 9

Human Farnesoid X Receptor (NR1H4, FXR) Reporter Assay

Determination of a ligand mediated Gal4 promoter driven transactivation to quantify ligand binding mediated activation of FXR. A FXR Reporter Assay kit was purchased from Indigo Bioscience (#IB00601-32) to determine the potency and efficacy of compounds that can induce FXR activation. The nuclear receptor assay system utilizes non-human mammalian cells engineered to provide constitutive high level expression of Human FXR receptor (NR1H4), a ligand-dependent transcription factor. The reporter cells include luciferase reporter gene functionality linked to an FXR-response promoter. Quantifying changes in luciferase expression in the treated reporter cells provides a sensitive surrogate measure of the changes in FXR activity.

The reporter cells incorporate the cDNA encoding beetle luciferase, a protein that catalyses the mono-oxidation of D-luciferin in a Mg$^{2+}$ dependent reaction that consumes O$_2$ and ATP as co-substrates, yielding the products Oxylucifern, AMP, PP$_i$, CO$_2$ and photon (light) emission. Luminescence intensity of the reaction is quantified using a luminometer, and is reported in terms of Relative Light Units (RLU's).

The assay was performed according to the manufacturer's instructions. In brief, the test compounds were weighed and dissolved in phosphate buffer solution as a 10 mM stock and diluted to the appropriate concentration using Compound Screening Medium (CSM). The frozen reporter cells were thawed and suspended in Cell Recovery Medium at 37° C. The compounds were then immediately added to the cell plate and the plate was placed into a 37° C., humidified CO$_2$ incubator for 22-24 h. After incubation, the media was carefully removed, Luciferase detection solution was added and the plate read in a Luminometer. The data was calculated as per kit instructions, with increases in luminescence being directly proportional to increases in compound agonist activity.

Table 1 summarizes the potency ranges for the compounds of the invention. The EC$_{50}$ values were determined using the Human FXR (NR1H4) assay and efficacy was normalized to GW4064 set as 100% (A=EC50<0.5 µM; B=0.5<EC50>5 µM; C=EC50>5 µM).

TABLE 1

Potency of compounds tested.

| Example | EC50 (µM) | Efficacy (%) |
|---|---|---|
| 4 | A | 94 |
| 5 | A | 111 |
| 6 | C | 96 |
| 7 | C | 89 |
| 8 | B | 127 |

Example 10

Metabolism in Human Microsomes

Microsomal mixes (247.5 µL) of human microsomes (1250 µL, 4 mg/ml), potassium phosphate buffer (1250 µL), alamethecin (12.5 µL, 5 mg/ml) and cofactors Nicotinamide Adenine Dinucleotide Phosphate NADPH (1250 µL, 4 mM)/ uridine 5'-diphospho-glucuronic acid UDPGA (1250 µL, 4 mM) or UDPGA only were loaded onto a shaker for 10 minutes. The test compound (2.5 µL, 100 µM) was then separately added to both microsomal mixes (i.e., one mix with NADPH and one mix without NADPH), incubated at 37° C. and sampled at predetermined time points. Analysis was performed using a AB SCIEX QTRAP 4500 LC-MS/MS, a Kinetex C18, 50*4.6 mm, 5 µm column and eluting with 10 mM Ammonium Acetate/Methanol.

Table 2 summarizes the % of compound remaining after 45 minutes of incubation with human microsomes either in the presence of co-factors UDPGA and NADPH or UDPGA only.

TABLE 2

Percent of compound remaining after 45 minutes of incubation.

| Compound of Example # | % remaining @ 45 mins of incubation with UDPGA and NADPH | % remaining @ 45 mins of incubation with UDPGA |
|---|---|---|
| 4 | 52 | 94 |
| 6 | 26 | 92 |
| 7 | 38 | 95 |

Significant metabolism by human microsomes only occurs in the presence of the co-factor NADPH, which shows that the compounds are metabolised via a cyp oxidation pathway. Stability of the compounds in the presence of the co-factor UDPGA shows that metabolism via acyl-glucuronidation is not occurring.

Example 11

Metabolic Identification in Hepatocytes.

A 10 mM stock of test compound from Example 4 (sodium 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-sulfinate) was prepared in DMSO. 20 µM of final working stock was then prepared by diluting 4 µL of 10 mM stock in 1996 µL of Krebs-Hensleit buffer. 200 µL of hepatocyte cell suspension (2×10$^6$ cells/mL) was added to TPP 48 well plate and preincubated for 30 min@37° C. in incubator. 200 µL of 20 µM working stock of test compound was added to the cell suspension and incubated in an incubator on vibramax at a shaking speed of 500 rpm. For the 0 min sample, 25 µL of hepatocyte suspension was precipitated with 200 µL of acetonitrile and 25 µL of 20 µM test compound was added. The reaction was stopped at 15, 30, 60, 90, 120 min by precipitating 50 µL of incubation mixture with 200 µL of acetonitrile. The samples were vortexed for 5 min at 1200 rpm and centrifuged at 4000 rpm for 10 min. The supernatant was separated, diluted 2 fold with water and analysed using a HPLC (Shimadzu SIL HTS) and mass spectrometer (5500 Qtrap). Acetonitrile and 0.1% formic acid in Milli-q-water were used as the mobile phase, using a column of either Waters Xbridge C18, 250× 3.0 mm, 5.0µ particle size or Phenomnex kinetex 5µ EVO C18 100 A, 50×4.6 mm 5.0µ particle size.

Table 3 summarizes the major metabolites observed when the compound of Example 4 of the invention was incubated in human, dog or mouse hepatocytes.

TABLE 3

Metabolic identification in hepatocytes with the compound of Example 4

| Species | Observed Major Metabolites | Acyl-Glucuronide |
| --- | --- | --- |
| Human | Hydroxy, Alkenyl and Alkenyl-hydroxy | No |
| Dog | Hydroxy, Di-hydroxy Alkenyl and Alkenyl-hydroxy | No |
| Mouse | Hydroxy, Di-hydroxy and Alkenyl-hydroxy | No |

FIG. 1 shows the MS/MS spectra of the major metabolites formed from the incubation of the compound of Example 4 with human hepatocytes for 120 mins The [M+H]$^+$ ion and fragmentation pattern are consistent with oxidative metabolism to give the corresponding hydroxy compound.

The incubation studies with microomse (Example 10) and hepatocytes (Example 11) show that the compounds tested are not metabolised via acyl-glucuronidation but rather via cyp oxidatation only. This is a different metabolic profile than a corresponding carboxylic acid compound which are typically metabolised to the acyl-glucuronide. Such metabolism can give rise to reactive metabolites that cause liver toxicity and drug induced liver injury (Shipkova M, Armstrong V W, Oellerich M, and Wieland E (2003) Acyl glucuronide drug metabolites: Toxicological and analytical implications. *Ther Drug Monit* 25: 1-16; Regan S, Maggs J, Hammond T, Lambert C, Williams D and Park B K (2010) Acyl glucuronides: the good, the bad and the ugly. *Biopharm Drug Dispos* 31: 367-395; Shipkova M, Armstrong V W, Oellerich M, and Wieland E (2003) Acyl glucuronide drug metabolites: Toxicological and analytical implications. *Ther Drug Monit* 25: 1-16).

Both classes of FXR agonists, derivatives of bile acids e.g., obeticholic acid and non-bile acids, commonly contain the carboxylic acid functionality and are metabolised via Phase 2 conjugation, such as acyl-glucuronidation, due to their inherent chemical properties (Center for Drug Evaluation and Research, *Application Number:* 2079990rig1s000, Pharmacology Review(s); Gege C, Hambruch E, Hambruch N, Kinzel O, Kremoser C. Nonsteroidal FXR Ligands: Current Status and Clinical Applications, *Handb Exp Pharmacol.* 2019 Jun. 14; Tully D C, Rucker P V, Chianelli D, Williams J, Vidal A, Alper P B, Mutnick D, Bursulaya B, Schmeits J, Wu X, Bao D, Zoll J, Kim Y, Groessl T, McNamara P, Seidel H M, Molteni V, Liu B, Phimister A, Joseph S B, Laffitte B., Discovery of_Tropifexor_(LJN452), a Highly Potent Non-bile Acid FXR Agonist for the Treatment of Cholestatic Liver Diseases and Nonalcoholic Steatohepatitis (NASH), *J Med Chem.* 2017 Dec. 28, 60(24), 9960-9973).

It is understood that the examples and embodiments described herein are for illustrative purposes only and that various modifications or changes in light thereof will be suggested to persons skilled in the art and are to be included within the spirit and purview of this application and scope of the appended claims.

That which is claimed is:

1. A compound having a structure of Formula II, VI or VII:

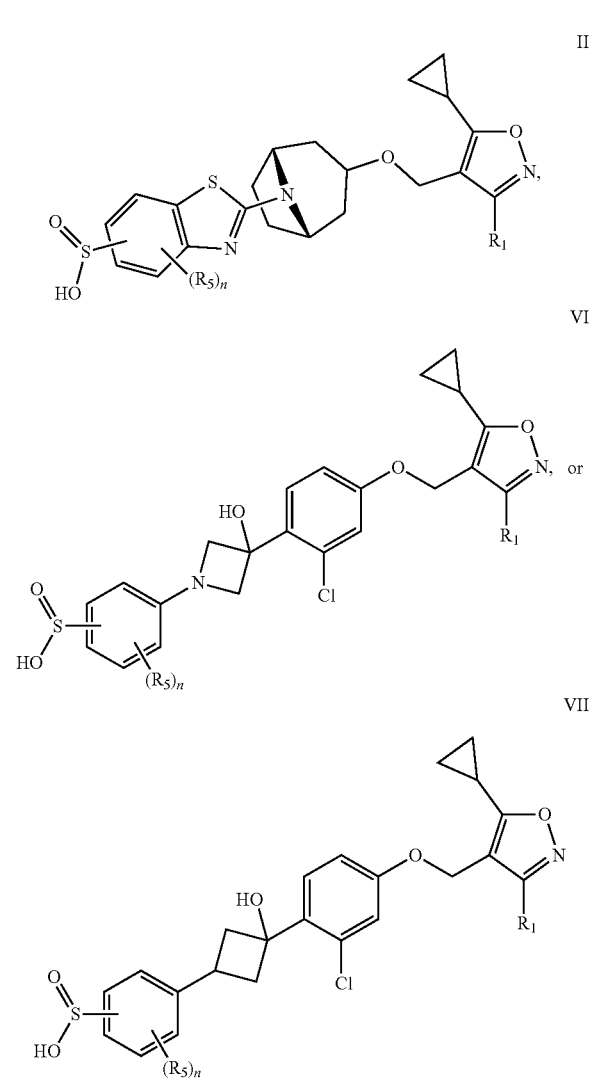

wherein:
R$_1$ is a C$_{3-10}$ cycloalkyl, phenyl or pyridyl that is optionally substituted with 1-3 R$_{1a}$;
each R$_{1a}$ is independently selected from the group consisting of a halogen, C$_{1-6}$ alkyl, haloC$_{1-6}$ alkyl, C$_{1-6}$ alkoxy, haloC$_{1-6}$ alkoxy and cyclopropyl;
each R$_5$ is independently selected from the group consisting of a C$_{1-6}$ alkyl, C$_{3-6}$ cycloalkyl, haloC$_{1-6}$ alkyl, C$_{1-6}$ alkoxy, haloC$_{1-6}$ alkoxy and halogen; and
n is an integer of 0, 1, 2 or 3; or
an enantiomer, stereoisomer, tautomer, solvate, hydrate or pharmaceutically acceptable salt thereof.

2. The compound of claim 1, wherein R$_1$ is phenyl optionally substituted with 1-3 R$_{1a}$, wherein each R$_{1a}$ is independently selected from the group consisting of a halogen, C$_{1-6}$ alkyl, haloC$_{1-6}$ alkyl, C$_{1-6}$ alkoxy, and haloC$_{1-6}$ alkoxy,
or
an enantiomer, stereoisomer, tautomer, solvate, hydrate, or pharmaceutically acceptable salt thereof.

3. The compound of claim 1 having a structure of Formula IIa:

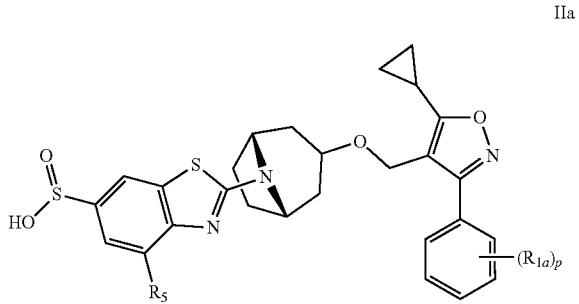

IIa wherein:
each $R_{1a}$ is independently selected from the group consisting of a halogen, trifluoromethyl, trifluoromethoxy and difluoromethoxy;
$R_5$ is methyl, methoxy, fluoro or trifluoromethoxy;
p is an integer of 0 or 1; or
an enantiomer, stereoisomer, tautomer, solvate, hydrate, or pharmaceutically acceptable salt thereof.

4. The compound of claim 1, wherein the compound is selected from the group consisting of sodium 2-(3-((5-cyclopropyl-3-(2-(trifluoromethoxy)phenyl)isoxazol-4-yl)methoxy)-8-azabicyclo[3.2.1]octan-8-yl)-4-fluorobenzo[d]thiazole-6-sulfinate, sodium 2-((1R,3r,5S)-3-((5-cyclopropyl-3-(2-(trifluoromethoxy)phenyl)isoxazol-4-yl)methoxy)-8-azabicyclo[3.2.1]octan-8-yl)-4-methylbenzo[d]thiazole-6-sulfinate, sodium 3-(3-(2-chloro-4-((5-cyclopropyl-3-(2,6-dichlorophenyl)isoxazol-4-yl)methoxy)phenyl)-3-hydroxyazetidin-1-yl)benzenesulfinate, sodium 4-(3-(2-chloro-4-((5-cyclopropyl-3-(2,6-dichlorophenyl)isoxazol-4-yl)methoxy)phenyl)-3-hydroxycyclobutyl)benzenesulfinate, and any combination thereof;
or an enantiomer, stereoisomer, tautomer, solvate, hydrate, or pharmaceutically acceptable salt thereof.

5. The compound of claim 1, wherein the compound has the structure of Formula II:

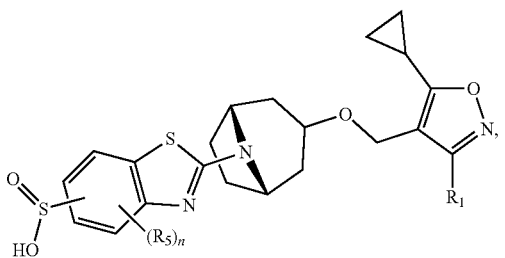

II wherein:
$R_1$ is a $C_{3-10}$ cycloalkyl, phenyl or pyridyl that is optionally substituted with 1-3 $R_{1a}$;
each $R_{1a}$ is independently selected from the group consisting of a halogen, $C_{1-6}$ alkyl, halo$C_{1-6}$ alkyl, $C_{1-6}$ alkoxy, halo$C_{1-6}$ alkoxy and cyclopropyl;
each $R_5$ is independently selected from the group consisting of a $C_{1-6}$ alkyl, $C_{3-6}$ cycloalkyl, halo$C_{1-6}$ alkyl, $C_{1-6}$ alkoxy, halo$C_{1-6}$ alkoxy and halogen; and
n is an integer of 0, 1, 2 or 3; or
an enantiomer, stereoisomer, tautomer, solvate, hydrate, or pharmaceutically acceptable salt thereof.

6. The compound of claim 1, wherein the compound has the structure of Formula VI:

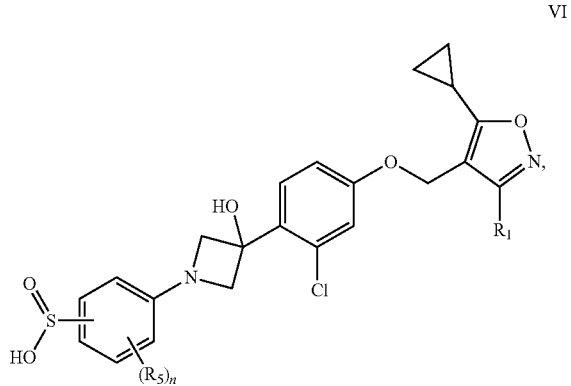

VI wherein:
$R_1$ is a $C_{3-10}$ cycloalkyl, phenyl or pyridyl that is optionally substituted with 1-3 $R_{1a}$;
each $R_{1a}$ is independently selected from the group consisting of a halogen, $C_{1-6}$ alkyl, halo$C_{1-6}$ alkyl, $C_{1-6}$ alkoxy, halo$C_{1-6}$ alkoxy and cyclopropyl;
each $R_5$ is independently selected from the group consisting of a $C_{1-6}$ alkyl, $C_{3-6}$ cycloalkyl, halo$C_{1-6}$ alkyl, $C_{1-6}$ alkoxy, halo$C_{1-6}$ alkoxy and halogen; and
n is an integer of 0, 1, 2 or 3; or
an enantiomer, stereoisomer, tautomer, solvate, hydrate, or pharmaceutically acceptable salt thereof.

7. The compound of claim 1, wherein the compound has the structure of Formula VII:

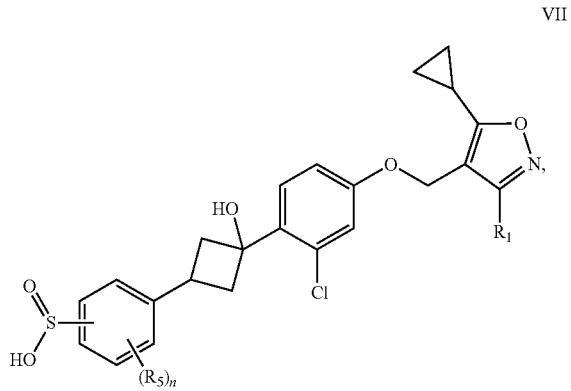

VII wherein:
$R_1$ is a $C_{3-10}$ cycloalkyl, phenyl or pyridyl that is optionally substituted with 1-3 $R_{1a}$;
each $R_{1a}$ is independently selected from the group consisting of a halogen, $C_{1-6}$ alkyl, halo$C_{1-6}$ alkyl, $C_{1-6}$ alkoxy, halo$C_{1-6}$ alkoxy and cyclopropyl;
each $R_5$ is independently selected from the group consisting of a $C_{1-6}$ alkyl, $C_{3-6}$ cycloalkyl, halo$C_{1-6}$ alkyl, $C_{1-6}$ alkoxy, halo$C_{1-6}$ alkoxy and halogen; and
n is an integer of 0, 1, 2 or 3; or
an enantiomer, stereoisomer, tautomer, solvate, hydrate, or pharmaceutically acceptable salt thereof.

8. The compound of claim 2, wherein $R_1$ is substituted with 1-3 $R_{1a}$, and wherein each $R_{1a}$ is independently selected from the group consisting of a halogen, $C_{1-6}$ alkyl, halo$C_{1-6}$ alkyl, $C_{1-6}$ alkoxy, and halo$C_{1-6}$ alkoxy.

9. The compound of claim 8, wherein each $R_{1a}$ is independently selected from the group consisting of a halogen, methoxy, methyl, trifluoromethyl, trifluoromethoxy and difluoromethoxy.

10. A pharmaceutical composition comprising the compound of claim 1 and a pharmaceutically acceptable carrier.

11. A pharmaceutical composition comprising the compound of claim 2 and a pharmaceutically acceptable carrier.

12. A pharmaceutical composition comprising the compound of claim 3 and a pharmaceutically acceptable carrier.

13. A pharmaceutical composition comprising the compound of claim 4 and a pharmaceutically acceptable carrier.

14. A method of treating a disease or disorder in a subject, the method comprising:
   administering the compound of claim 1 to the subject, thereby treating and/or preventing the disease or disorder in the subject,
   wherein the disease or disorder is selected from the group consisting of a bile acid related disorder, metabolic syndrome, type-2 diabetes, diabetic nephropathy, hyperlipidemia, hypertriglyceridemia, obesity, liver cirrhosis, primary biliary cirrhosis (PBC), primary sclerosing cholangitis (PSC), fatty liver disease, nonalcoholic steatohepatitis (NASH), nonalcoholic fatty liver disease (NAFLD), alcoholic liver disease, chemotherapy associated steatohepatitis (CASH), hepatitis B, inflammatory autoimmune diseases, inflammatory bowel disease, Crohn's disease, ulcerative colitis, proctitis, pouchitis, Celiac's Disease, bile acid diarrhea, multiple sclerosis, atherosclerosis, kidney disorders, and cancer.

15. A method of treating a disease or disorder in a subject, the method comprising:
   administering the compound of claim 2 to the subject, thereby treating and/or preventing the disease or disorder in the subject,
   wherein the disease or disorder is selected from the group consisting of a bile acid related disorder, metabolic syndrome, type-2 diabetes, diabetic nephropathy, hyperlipidemia, hypertriglyceridemia, obesity, liver cirrhosis, primary biliary cirrhosis (PBC), primary sclerosing cholangitis (PSC), fatty liver disease, nonalcoholic steatohepatitis (NASH), nonalcoholic fatty liver disease (NAFLD), alcoholic liver disease, chemotherapy associated steatohepatitis (CASH), hepatitis B, inflammatory autoimmune diseases, inflammatory bowel disease, Crohn's disease, ulcerative colitis, proctitis, pouchitis, Celiac's Disease, bile acid diarrhea, multiple sclerosis, atherosclerosis, kidney disorders, and cancer.

16. A method of treating a disease or disorder in a subject, the method comprising:
   administering the compound of claim 3 to the subject, thereby treating and/or preventing the disease or disorder in the subject,
   wherein the disease or disorder is selected from the group consisting of a bile acid related disorder, metabolic syndrome, type-2 diabetes, diabetic nephropathy, hyperlipidemia, hypertriglyceridemia, obesity, liver cirrhosis, primary biliary cirrhosis (PBC), primary sclerosing cholangitis (PSC), fatty liver disease, nonalcoholic steatohepatitis (NASH), nonalcoholic fatty liver disease (NAFLD), alcoholic liver disease, chemotherapy associated steatohepatitis (CASH), hepatitis B, inflammatory autoimmune diseases, inflammatory bowel disease, Crohn's disease, ulcerative colitis, proctitis, pouchitis, Celiac's Disease, bile acid diarrhea, multiple sclerosis, atherosclerosis, kidney disorders, and cancer.

17. A method of treating a disease or disorder in a subject, the method comprising:
   administering the compound of claim 4 to the subject, thereby treating and/or preventing the disease or disorder in the subject,
   wherein the disease or disorder is selected from the group consisting of a bile acid related disorder, metabolic syndrome, type-2 diabetes, diabetic nephropathy, hyperlipidemia, hypertriglyceridemia, obesity, liver cirrhosis, primary biliary cirrhosis (PBC), primary sclerosing cholangitis (PSC), fatty liver disease, nonalcoholic steatohepatitis (NASH), nonalcoholic fatty liver disease (NAFLD), alcoholic liver disease, chemotherapy associated steatohepatitis (CASH), hepatitis B, inflammatory autoimmune diseases, inflammatory bowel disease, Crohn's disease, ulcerative colitis, proctitis, pouchitis, Celiac's Disease, bile acid diarrhea, multiple sclerosis, atherosclerosis, kidney disorders, and cancer.

\* \* \* \* \*

UNITED STATES PATENT AND TRADEMARK OFFICE
CERTIFICATE OF CORRECTION

PATENT NO. : 11,339,153 B2
APPLICATION NO. : 17/265266
DATED : May 24, 2022
INVENTOR(S) : Sharma et al.

Page 1 of 3

It is certified that error appears in the above-identified patent and that said Letters Patent is hereby corrected as shown below:

On the Title Page

Item (56) References Cited, FOREIGN PATENT DOCUMENTS:
Please correct "DE 2545964 A1*" to read --EP 2545964 A1*--

In the Specification

Column 5, Formula VII, Lines 1-15: Please delete Formula VII and replace with the following:

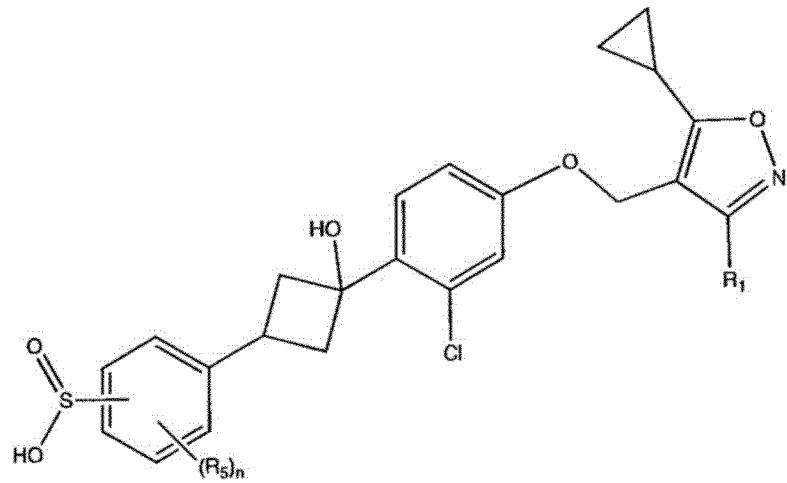

VII

Signed and Sealed this
Thirtieth Day of May, 2023

Katherine Kelly Vidal
*Director of the United States Patent and Trademark Office*

CERTIFICATE OF CORRECTION (continued)
U.S. Pat. No. 11,339,153 B2

Column 5, Formula VIII, Lines 16-33: Please delete Formula VIII and replace with the following:

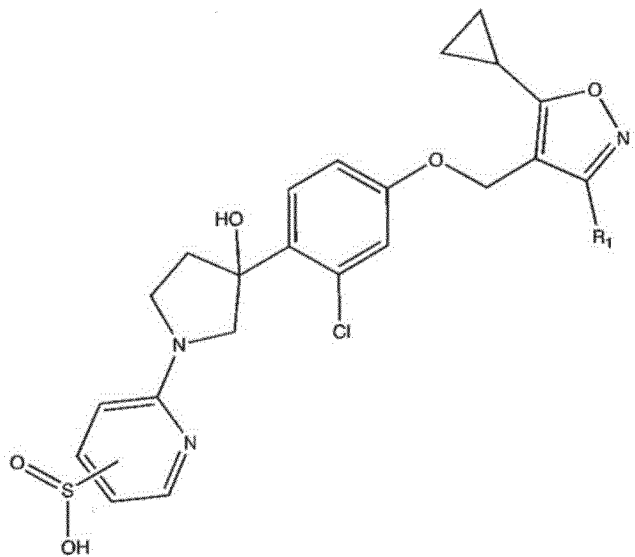

VIII

Column 7, Line 22: Please correct "farnesoid X" to read --farnesoid X--

Column 18, Formula VII, Lines 1-15: Please delete Formula VII and replace with the following:

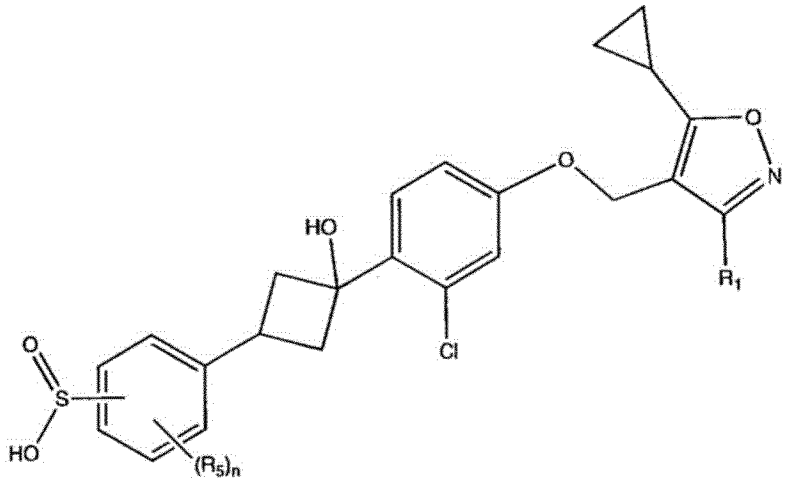

VII

Column 18, Formula VIII, Lines 16-33: Please delete Formula VIII and replace with the following:
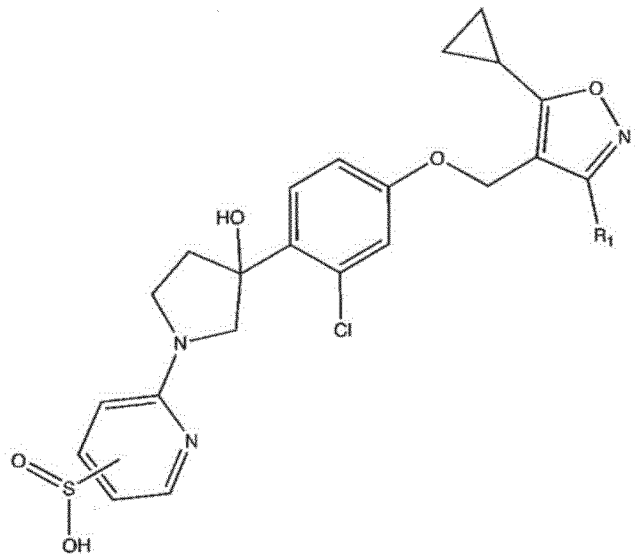
VIII